US012714764B2

(12) United States Patent
Ihara

(10) Patent No.: US 12,714,764 B2
(45) Date of Patent: Aug. 25, 2026

(54) FRAGRANCE PRESENTATION DEVICE, FRAGRANCE PRESENTATION SYSTEM, AND MANAGEMENT DEVICE

(71) Applicant: SONY GROUP CORPORATION, Tokyo (JP)

(72) Inventor: Tetsugorou Ihara, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 916 days.

(21) Appl. No.: 18/001,743

(22) PCT Filed: Jun. 11, 2021

(86) PCT No.: PCT/JP2021/022322

§ 371 (c)(1),
(2) Date: Dec. 14, 2022

(87) PCT Pub. No.: WO2021/261296

PCT Pub. Date: Dec. 30, 2021

(65) Prior Publication Data

US 2023/0241278 A1 Aug. 3, 2023

(30) Foreign Application Priority Data

Jun. 22, 2020 (JP) ................................ 2020-106946

(51) Int. Cl.
*A61L 2/00* (2006.01)
*A01G 27/00* (2006.01)
(Continued)

(52) U.S. Cl.
CPC ............... *A61L 9/122* (2013.01); *A61L 9/035* (2013.01); *A61L 9/125* (2013.01); *G09F 27/00* (2013.01);
(Continued)

(58) Field of Classification Search
CPC ... A61L 9/125; A61L 9/14; A61L 9/01; A61L 2209/13; A61L 2209/133; B01F 3/04
(Continued)

(56) References Cited

U.S. PATENT DOCUMENTS 6,554,203 B2 * 4/2003 Hess ......................... A61L 9/14 239/69
6,556,272 B1 4/2003 Du et al.
(Continued)

FOREIGN PATENT DOCUMENTS

JP 08-106288 A 4/1996
JP 09-327506 A 12/1997
(Continued)

OTHER PUBLICATIONS

International Search Report and Written Opinion of PCT Application No. PCT/JP2021/022322, issued on Aug. 31, 2021, 12 pages of ISRWO.

*Primary Examiner* — Monzer R Chorbaji
(74) *Attorney, Agent, or Firm* — CHIP LAW GROUP

(57) ABSTRACT

Provided is a fragrance presentation device (100) that presents a fragrance in conjunction with content including at least one element of a sound, a music, an image, a video, and a tactile stimulation. The fragrance presentation device includes a housing unit (104) that houses a cartridge containing one or a plurality of aromas, and a discharge unit (106) that discharges the aroma. The fragrance presentation device (100) discharges the aroma in synchronization with an output of the content according to the aroma score including at least one element of an aroma type, an aroma generation timing, a discharge duration, a discharge amount, a discharge pattern, and a discharge trigger.

10 Claims, 23 Drawing Sheets

(51) Int. Cl.

| | |
|---|---|
| ***A61L 9/03*** | (2006.01) |
| ***A61L 9/12*** | (2006.01) |
| ***B01D 47/00*** | (2006.01) |
| ***G09F 27/00*** | (2006.01) |
| *G06K 19/06* | (2006.01) |

(52) U.S. Cl.
CPC .... *A61L 2209/111* (2013.01); *A61L 2209/133* (2013.01); *A61L 2209/134* (2013.01); *G06K 19/06037* (2013.01)

(58) Field of Classification Search
USPC .............. 422/5, 120, 123, 305–306; 239/69; 261/30
See application file for complete search history.

(56) References Cited

U.S. PATENT DOCUMENTS

| | | | | |
|---|---|---|---|---|
| 2020/0078485 | A1* | 3/2020 | Suarez Iribarne ...... | A61L 9/125 |
| 2020/0084411 | A1* | 3/2020 | Kim ........................ | A61L 9/125 |

FOREIGN PATENT DOCUMENTS

| | | | |
|---|---|---|---|
| JP | 2007-130255 | A | 5/2007 |
| JP | 2009-049746 | A | 3/2009 |
| JP | 5288573 | B1 | 9/2013 |
| JP | 2015-125580 | A | 7/2015 |
| JP | 6552696 | B1 | 7/2019 |

* cited by examiner

Contents ID:a37d5hr8

Contents ID:a37d5hr8

| T001010 | T0003 | A0302 | I07 | PB | T003035 | T0040 | A0301 | I06 | PB | ··· |
|---|---|---|---|---|---|---|---|---|---|---|

Figure 16:
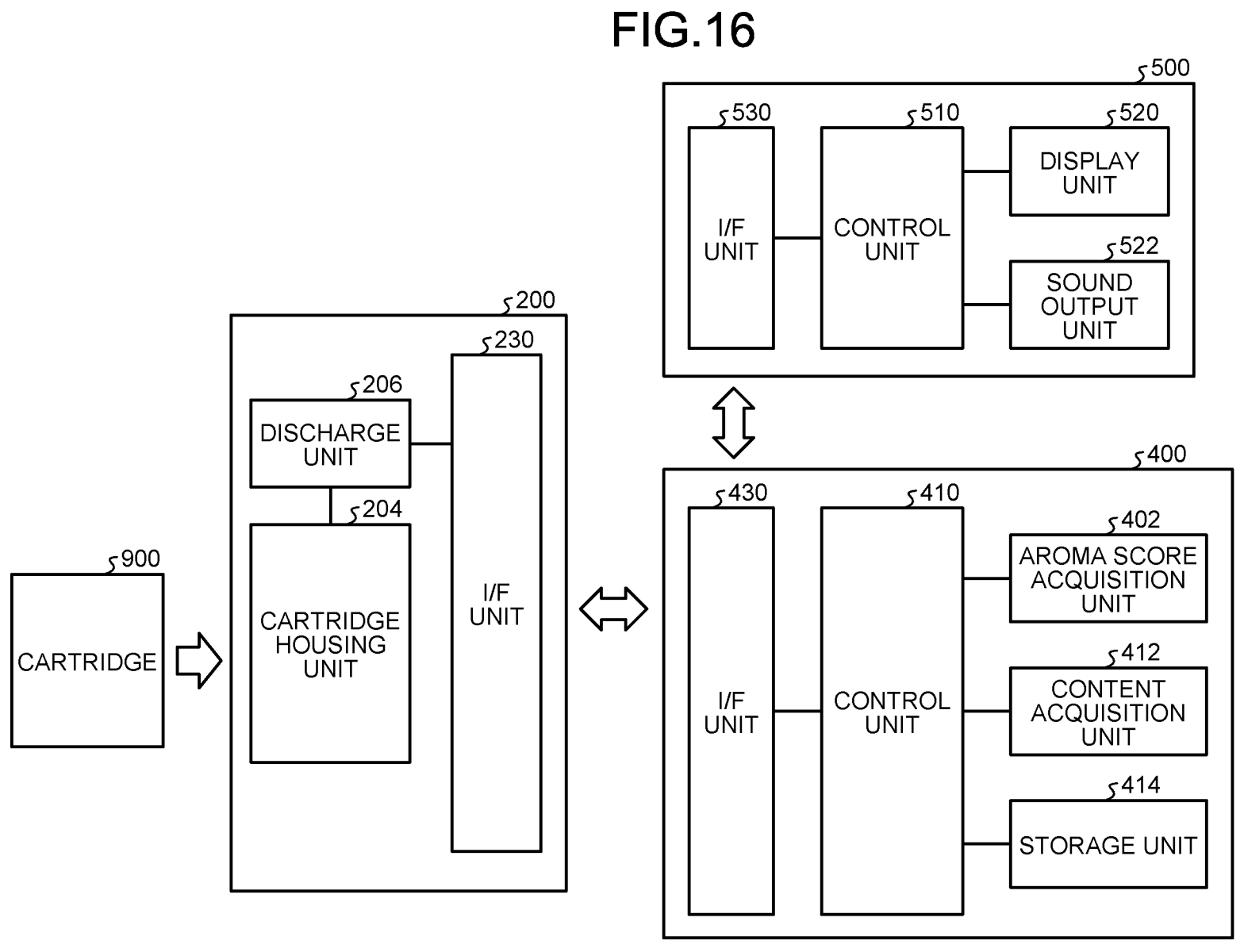

500
520 DISPLAY UNIT
522 SOUND OUTPUT UNIT
510 CONTROL UNIT
530 I/F UNIT 400
402 AROMA SCORE ACQUISITION UNIT
412 CONTENT ACQUISITION UNIT
414 STORAGE UNIT
410 CONTROL UNIT
430 I/F UNIT 200
230 I/F UNIT
206 DISCHARGE UNIT
204 CARTRIDGE HOUSING UNIT

900 CARTRIDGE 600
640
SENSOR UNIT
610
CONTROL UNIT
630
I/F UNIT
300a
302
AROMA SCORE ACQUISITION UNIT
312
CONTENT ACQUISITION UNIT
314
STORAGE UNIT
320
DISPLAY UNIT
322
SOUND OUTPUT UNIT
318
ADJUSTMENT UNIT
310
CONTROL UNIT
330
I/F UNIT
200
230
I/F UNIT
204
DISCHARGE UNIT
202
CARTRIDGE HOUSING UNIT
800
CARTRIDGE

FIG.24

Sub Aroma Score ID:Seaside

| Seaside | PARAMETER |
|---|---|
| ID | st1245 |
| DISCHARGE DURATION | 0.2s |
| AROMA TYPE | 5rd-(2) |
| DISCHARGE AMOUNT (INTENSITY) | 4/10 |
| DISCHARGE PATTERN | D |
| TRIGGER SETTING | XXX |
| ... | ... |

Sub Aroma Score ID:Rose

| Seaside | PARAMETER |
|---|---|
| ID | st0549 |
| DISCHARGE DURATION | 0.5s |
| AROMA TYPE | 1rd-(2) |
| DISCHARGE AMOUNT (INTENSITY) | 9/10 |
| DISCHARGE PATTERN | A |
| TRIGGER SETTING | XXX |
| ... | ... |

FRAGRANCE PRESENTATION DEVICE, FRAGRANCE PRESENTATION SYSTEM, AND MANAGEMENT DEVICE

CROSS REFERENCE TO RELATED APPLICATIONS

This application is a U.S. National Phase of International Patent Application No. PCT/JP2021/022322 filed on Jun. 11, 2021, which claims priority benefit of Japanese Patent Application No. JP 2020-106946 filed in the Japan Patent Office on Jun. 22, 2020. Each of the above-referenced applications is hereby incorporated herein by reference in its entirety.

FIELD

The present disclosure relates to a fragrance presentation device, a fragrance presentation system, and a management device.

BACKGROUND

In recent years, there has been developed a technique to provide (present) a fragrance that is difficult to distribute itself as digital information when reproducing content such as a video. Examples of the technique are disclosed in Patent Literatures 1 and 2 below.

CITATION LIST

Patent Literature

Patent Literature 1: JP 2015-125580 A
Patent Literature 2: JP 2009-049746 A

SUMMARY

Technical Problem

In the techniques disclosed in Patent Literatures 1 and 2, control data for presenting a fragrance to a user is distributed as data integrated with content data, and an aroma can be discharged at the time of reproducing content by using the control data. Therefore, when the user wants to enjoy the fragrance provided together with the content using the above-described techniques, dedicated content data is limited to the content prepared in advance, or the use of a dedicated system or the like is required. Therefore, it is difficult to easily enjoy an entertainment that also presents the fragrance together with the content, and spreading of such entertainment has been prevented.

Therefore, the present disclosure proposes a fragrance presentation device, a fragrance presentation system, and a management device capable of easily enjoying an entertainment that presents the fragrance together with the content.

Solution to Problem

According to the present disclosure, a fragrance presentation device that presents a fragrance in conjunction with content including at least one element of a sound, a music, an image, a video, and a tactile stimulation, is provided. The fragrance presentation device includes a housing unit configured to house a cartridge containing an aroma, the aroma being one or a plurality of aromas; and a discharge unit configured to discharge the aroma. The fragrance presentation device discharges the aroma, according to an aroma score, in synchronization with an output of the content. The aroma score includes at least one element of an aroma type, an aroma generation timing, a discharge duration, a discharge amount, a discharge pattern, and a discharge trigger.

Moreover, according to the present disclosure, a fragrance presentation system that presents a fragrance in conjunction with content including at least one element of a sound, a music, an image, a video, and a tactile stimulation, is provided. The fragrance presentation system includes a fragrance presentation device and an information processing apparatus. The fragrance presentation device includes a housing unit configured to house a cartridge containing an aroma, the aroma being one or a plurality of aromas, and a discharge unit configured to discharge the aroma. The information processing apparatus includes: an acquisition unit communicably connected to the fragrance presentation device and configured to acquire an aroma score including at least one element of an aroma type, an aroma generation timing, a discharge duration, a discharge amount, a discharge pattern and a discharge trigger, an output unit configured to output the content, and a control unit configured to control the discharge unit so as to discharge the aroma, according to the aroma score, in synchronization with an output of the content.

Moreover, according to the present disclosure, a management device that manages an aroma score used in a fragrance presentation device that presents an aroma in conjunction with content including at least one element of a sound, a music, an image, a video, and a tactile stimulation, is provided. The management device includes a storage unit configured to store the aroma score, in association with identification information of the content, including information designating at least one element of an aroma type, an aroma generation timing, a discharge duration, a discharge amount, a discharge pattern, and a discharge trigger, the aroma score being a variable-length data array including a plurality of characters or numbers.

BRIEF DESCRIPTION OF DRAWINGS

FIG. 10 is an explanatory diagram illustrating a configuration example of functional blocks of a fragrance presentation device 100*a* according to the second embodiment.

FIG. 11 is a flowchart illustrating an example of a processing method according to the second embodiment.

FIG. 16 is an explanatory diagram illustrating a configuration example of functional blocks of the fragrance presentation device 200, a game machine 400, and an HMD 500 according to a modification of the third embodiment.

FIG. 24 is an explanatory diagram illustrating a sub-aroma score according to a sixth embodiment of the present disclosure.

FIG. 29 is a hardware configuration diagram illustrating an example of a computer 1000 that implements functions of the information processing terminal 300 and the like.

DESCRIPTION OF EMBODIMENTS

Figure 1:
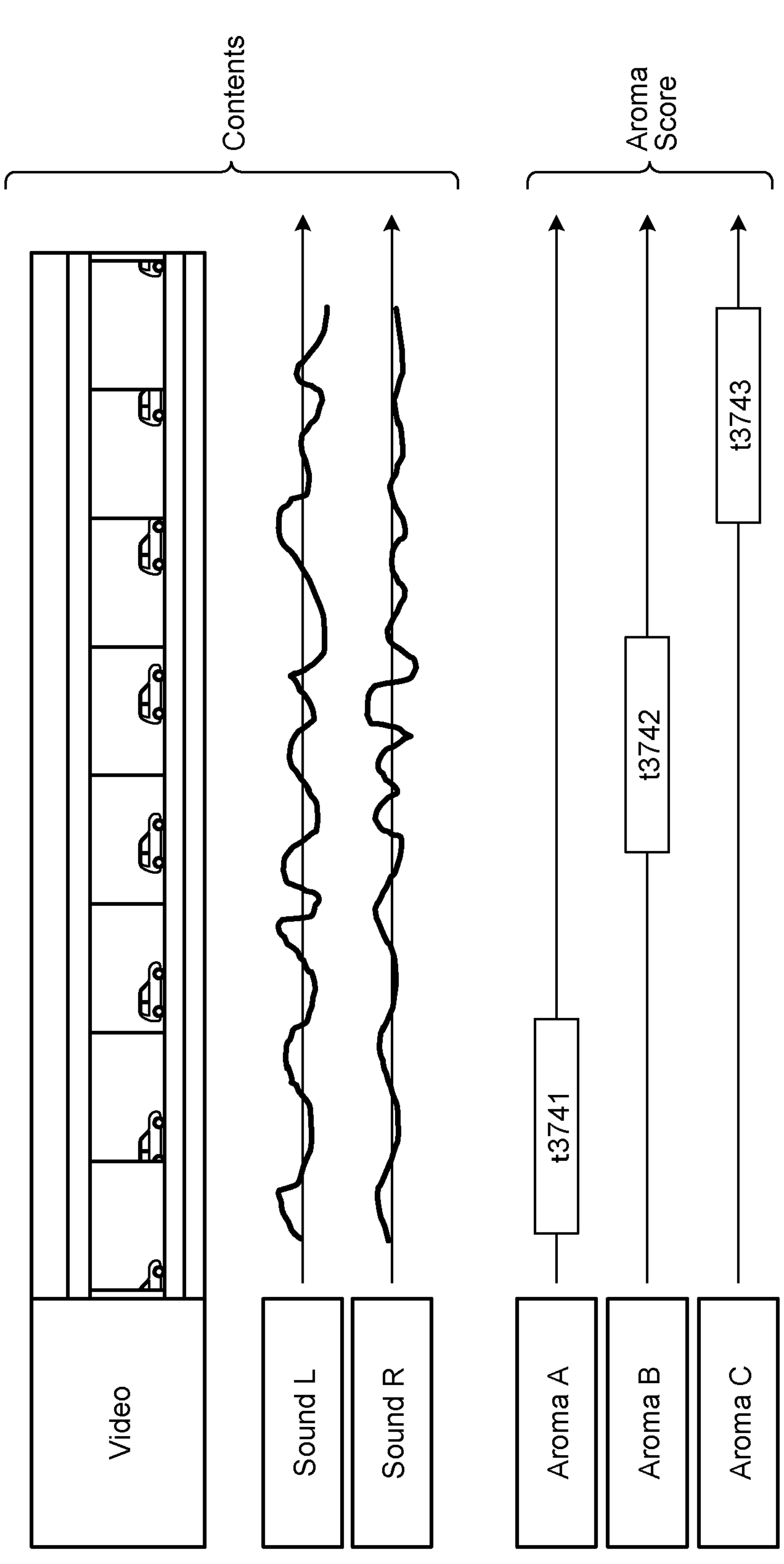
FIG. 1 is an explanatory diagram (part 1) illustrating an aroma score according to embodiments of the present disclosure.

Hereinafter, preferred embodiments of the present disclosure will be described in detail with reference to the accompanying drawings. Note that, in the present specification and the drawings, components having substantially the same functional configuration are denoted by the same reference signs to omit redundant description. In addition, in the present specification and the drawings, a plurality of components having substantially the same functional configurations may be distinguished by attaching a different alphabet after the same reference sign. However, when it is not particularly necessary to distinguish each of the plurality of components having substantially the same or similar functional configuration, only the same reference sign is assigned.

The description will be given in the following order.

1. Outline of embodiments of present disclosure
2. First Embodiment
2.1 Fragrance presentation system
2.2 Fragrance presentation device
2.3 Processing method
3. Second Embodiment
3.1 Fragrance presentation device
3.2 Processing method
4. Third Embodiment
4.1 Fragrance presentation device
4.2 Information processing terminal
4.3 Processing method
4.4 Modification
5. Fourth Embodiment
5.1 Information processing terminal
5.2 Biological information sensor
5.3 Processing method
5.4 Modification
6. Fifth Embodiment
6.1 Server
6.2 Classification unit
7. Sixth Embodiment
7.1 Generator
7.2 Processing method
7.3 Modification
8. Summary
9. Hardware configuration
10. Supplement

1. Outline of Embodiments of Present Disclosure

Figures 2, 3:
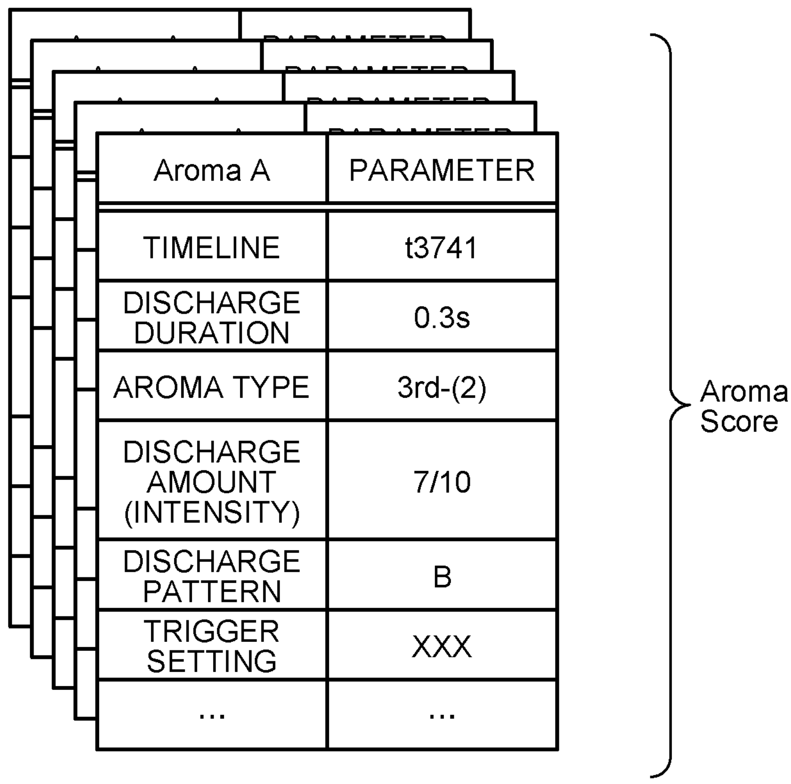
FIG. 2 is an explanatory diagram (part 2) illustrating the aroma score according to the embodiments of the present disclosure.
FIG. 3 is an explanatory diagram (part 3) illustrating the aroma score according to the embodiments of the present disclosure.

First, before describing details of embodiments of the present disclosure, the background leading to the creation of the embodiments of the present disclosure by the inventor and the outline of the embodiments of the present disclosure will be described with reference to FIGS. 1 to 3. FIGS. 1 to 3 are explanatory diagrams illustrating an aroma score according to the embodiments of the present disclosure.

As described above, in the techniques disclosed in Patent Literatures 1 and 2, control data for presenting a fragrance to a user is distributed as data integrated with content data, and the aroma can be discharged at the time of reproducing content by using the control data. Therefore, when the user wants to enjoy the fragrance provided together with the content using the above-described techniques, dedicated content data is limited to the content prepared in advance, or the use of a dedicated system or the like is required. Therefore, it is difficult to easily enjoy an entertainment that also presents the fragrance together with the content, and spreading of such entertainment has been prevented.

Therefore, in order to promote the spread, the inventor has created embodiments related to a fragrance presentation device, a fragrance presentation system, and a management device that enable the user to easily enjoy the entertainment as described above. According to the embodiments created by the inventor, even in the case of existing content such as a movie, the fragrance can be presented in synchronization with the content at the time of reproducing the content. Specifically, in the present embodiments, the content data for reproducing a video or the like, the control data for presenting the fragrance to the user, and a cartridge containing an aroma are separately provided to the user. In this way, according to the present embodiments, even in the case of existing content, the user can easily enjoy the fragrance together with the content at home or the like, and furthermore, can fully obtain realistic and immersive experiences. Furthermore, in the present embodiments, since the existing content can be used, a vast amount of content can be enjoyed as described above, and a range of entertainment that can be provided to the user is further broadened. As a result, the spread of this type of entertainment can be promoted.

In the following description, the embodiments of the present disclosure will be described as being applied to an entertainment in which a fragrance is presented together with content such as a movie including video and sound. However, the embodiments of the present disclosure are not limited thereto.

In the embodiments of the present disclosure, for example, when the content such as a movie including video and sound is reproduced, the aroma can be discharged in synchronization with the reproduction of the content. Specifically, as illustrated in FIG. 1, when the content data including video and sound (Sound L, Sound R) exists as existing content, control data for controlling the fragrance presentation device is prepared in order to discharge the aroma in synchronization with the reproduction of the content data. In the present specification, the control data is referred to as an "aroma score".

In an example illustrated in FIG. 1, the aroma score includes the control data of three fragrance patterns (Aroma A, Aroma B, and Aroma C), and the fragrance presentation device can discharge the aroma in synchronization with the reproduction (output) of the content by being controlled sequentially according to the three fragrance patterns similar to reading a music score.

As illustrated in FIG. 2, each discharge pattern includes information designating at least one of a type and a percentage of an aroma to be discharged (aroma type and aroma component), a timing to discharge the aroma (aroma generation timing) (timeline), a discharge duration (fragrance duration), a discharge amount (discharge amount is set stepwise in the example in FIG. 2), a discharge pattern (fragrance method), a discharge trigger in the content (trigger setting) (e.g., a page turning operation is set as a trigger when the content is an electronic book), and the like. In addition, the aroma score is linked to the content on a time axis. In the present embodiments, by handling the control data for fragrance in the form of an independent aroma score, it is possible to associate the fragrance presented together with a cartridge containing aroma (details will be described later) and the content data that are separately managed. In the present embodiments, as illustrated in FIG. 3, the aroma score including one or a plurality of discharge patterns may be converted, according to a predetermined rule, into a variable-length data array including a plurality of characters, numbers, or symbols. Furthermore, in the present embodiments, although details will be described later, the aroma score may be one-dimensionally or two-dimensionally coded data. In this way, the management, handling, processing, and the like of the aroma score can be facilitated, and the convenience of the user can be improved.

Furthermore, in the present embodiments, the aroma score can be associated with, for example, content identification information and distributed separately from the content data related to the content. Hereinafter, details of embodiments of the present disclosure created by the inventor will be sequentially described.

2. First Embodiment

<2.1 Fragrance Presentation System>

Figure 4:
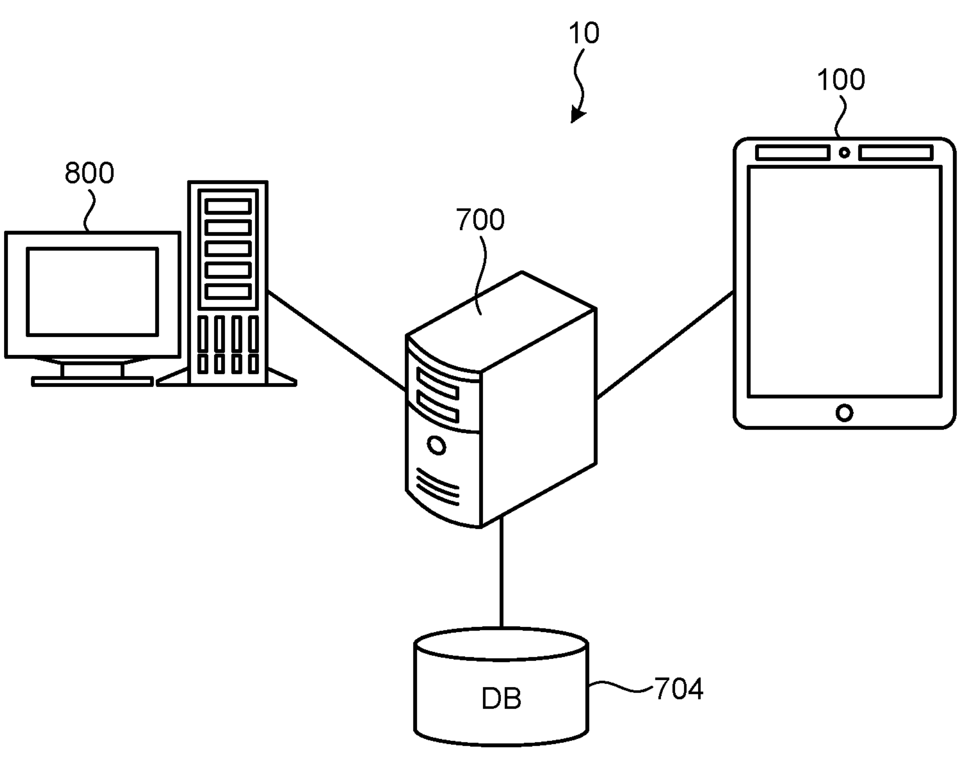
FIG. 4 is an explanatory diagram illustrating a configuration example of a fragrance presentation system 10 according to a first embodiment of the present disclosure.

First, a configuration example of a fragrance presentation system 10 according to a first embodiment of the present disclosure will be described with reference to FIG. 4. FIG. 4 is an explanatory diagram illustrating the configuration example of the fragrance presentation system 10 according to the first embodiment of the present disclosure. As illustrated in FIG. 4, the fragrance presentation system 10 according to the present embodiment can include, for example, a fragrance presentation device 100, a server 700, and a generator 800. The fragrance presentation device 100 and the server 700, and the server 700 and the generator 800 may be communicably connected to each other through various wired or wireless communication networks. In addition, the number of fragrance presentation devices 100 included in the fragrance presentation system 10 according to the present embodiment is not limited to the number illustrated in FIG. 4, and may include more. Furthermore, the fragrance presentation system 10 according to the present embodiment may include another server (not illustrated). Hereinafter, an outline of each device included in the fragrance presentation system 10 according to the present embodiment will be described.

(Fragrance Presentation Device 100)

The fragrance presentation device 100 can present a fragrance to the user in conjunction with content including at least one element from sound, music, image, video, and tactile stimulation. Specifically, the fragrance presentation device 100 can discharge the aroma in synchronization with an output of the content according to the aroma score associated with the content. Furthermore, in the present embodiment, the fragrance presentation device 100 can reproduce content including at least a moving image, music, tactile stimulation (vibration, wind), and the like, and output the content to the user. A detailed configuration of the fragrance presentation device 100 will be described later.

(Server 700)

The server 700 is a computer that can manage the above-described aroma score. Specifically, the server 700 can distribute the aroma score to the fragrance presentation device 100. Note that a detailed configuration of the server 700 will be described in an embodiment to be described later.

(Generator 800)

The generator 800 is a computer capable of generating the aroma score used by the fragrance presentation device 100 that presents the fragrance to the user together with content. Specifically, the generator 800 can generate the aroma score to provide the aroma score to the server 700 and the fragrance presentation device 100. Note that a detailed configuration of the generator 800 will be described in the embodiment to be described later.

In the present embodiment, two or all of the fragrance presentation device 100, the server 700, and the generator 800 may be an integrated device, and may not be realized by individual devices. For example, each of the fragrance presentation device 100, the server 700, and the generator 800 described above may be realized by a plurality of devices connected via various wired or wireless communication networks and cooperating with each other. Furthermore, the server 700 or the generator 800 described above can be realized by, for example, a hardware configuration of an information processing apparatus 1000 described later.

<2.2 Fragrance Presentation Device>

Figure 5:
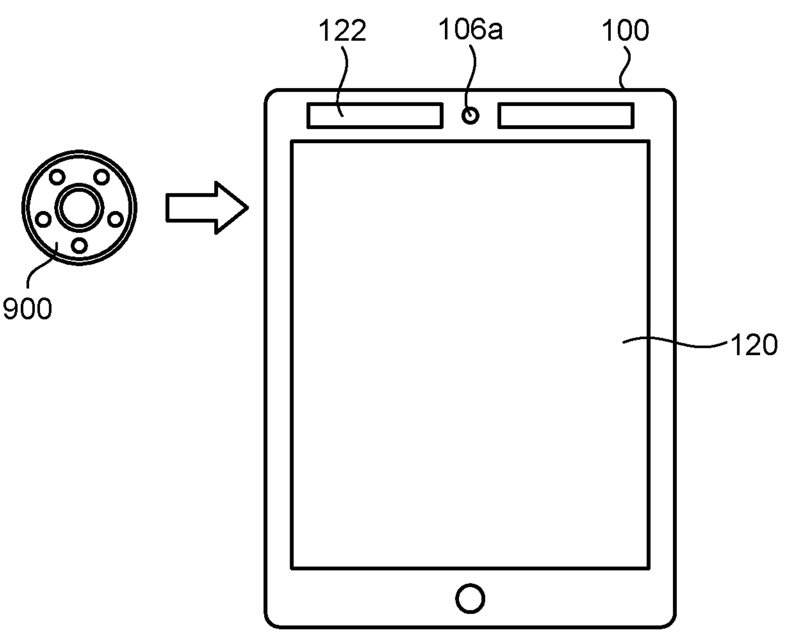
FIG. 5 is an explanatory diagram illustrating an appearance example of a fragrance presentation device 100 according to the first embodiment.

Next, a detailed configuration of the fragrance presentation device 100 according to the present embodiment will be described with reference to FIGS. 5 and 6. FIG. 5 is an explanatory diagram illustrating an appearance example of the fragrance presentation device 100 according to the present embodiment, and FIG. 6 is an explanatory diagram illustrating a configuration example of functional blocks of the fragrance presentation device 100 according to the present embodiment.

The fragrance presentation device 100 according to the present embodiment is an integrated device capable of presenting a fragrance and outputting content by the same device. Specifically, as illustrated in FIG. 5, a cartridge 900 containing one or a plurality of aromas is detachably housed in the fragrance presentation device 100 according to the present embodiment, and the aroma in the cartridge 900 is discharged through a discharge port 106*a* provided on a surface of the fragrance presentation device 100. The fragrance presentation device 100 further includes, on a surface thereof, a display unit 120 for displaying the content such as a moving image, and a sound output unit 122 for outputting the content such as music.

Figure 6:
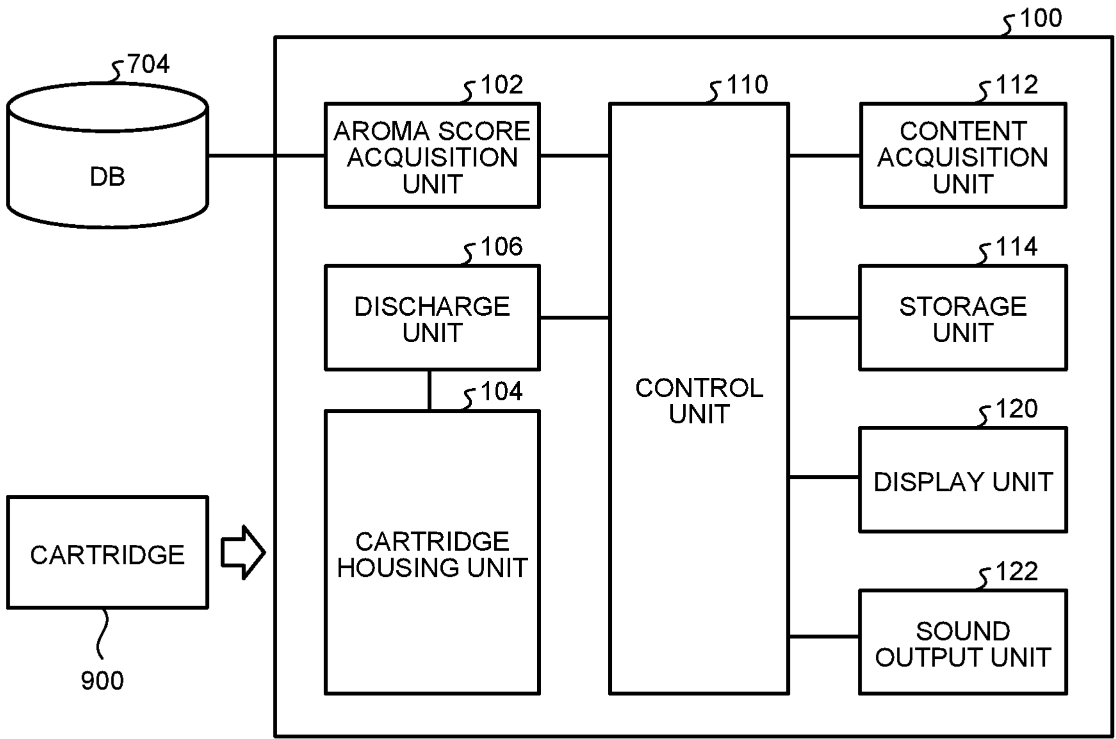
FIG. 6 is an explanatory diagram illustrating a configuration example of functional blocks of the fragrance presentation device 100 according to the first embodiment.

More specifically, as illustrated in FIG. 6, the fragrance presentation device 100 according to the present embodiment mainly includes an aroma score acquisition unit (acquisition unit) 102, a cartridge housing unit (housing unit) 104, a discharge unit 106, a control unit 110, a content acquisition unit 112, a storage unit 114, a display unit (output unit) 120, and a sound output unit (output unit) 122. Hereinafter, each functional block of the fragrance presentation device 100 will be sequentially described.

(Aroma Score Acquisition Unit 102)

The aroma score acquisition unit 102 acquires the aroma score that is associated with content identification information and designates at least one of the aroma, a discharge timing, a discharge duration, a discharge amount, and a discharge method from a database (DB) 704 or the like stored in, for example, the server 700 described later. For example, the user inputs the identification information of the content to an input unit (not illustrated) of the fragrance presentation device 100, and the aroma score acquisition unit 102 acquires the aroma score based on the input identification information. Furthermore, the aroma score acquisition unit 102 can output the aroma score acquired to the control unit 110. As described above, the aroma score is the control data used when the fragrance presentation device 100 presents the fragrance to the user together with the content.

(Cartridge Housing Unit 104)

For example, the cartridge housing unit 104 can detachably house the cartridge 900 including one or more aroma liquids that are essential oil or essential oil diluted by ethanol. In the present embodiment, the cartridge 900 is managed in association with predetermined identification information. Furthermore, in the present embodiment, the cartridge 900 may be a dedicated cartridge for each content, or may be the cartridge 900 that can be shared by a plurality of pieces of content belonging to a predetermined group. Thus, the cartridge 900 is not particularly limited.

In the present embodiment, it is preferable that the cartridge 900 contains a plurality of aromas so as to be able to support any content. For example, the fragrance presentation device 100 can discharge one aroma in the cartridge 900 or discharge the plurality of aromas in combination according to the content. Further, in the present embodiment, since the plurality of aromas can be provided to the user in the form of the cartridge 900, handling and distribution of the aromas can be facilitated. When the aromas are stored in advance in the fragrance presentation device 100 in order to discharge a wide variety of aromas according to any content, it is necessary to secure a large space for housing the aromas, and thus it is inevitable that the size of the fragrance presentation device 100 becomes large. Furthermore, in the case of a mode in which the aromas are required to be stored in advance, there is a limit to types of aromas that can be stored. On the other hand, in the present embodiment, for example, the cartridge 900 corresponding to specific content is mounted on the fragrance presentation device 100 instead of the mode in which the aromas are stored in advance in the fragrance presentation device 100. In this way, in the present embodiment, it is possible to present the fragrance corresponding to each piece of content without limitation in aroma types. In addition, it is possible to reduce the size of the fragrance presentation device 100.

More specifically, in the present embodiment, for example, an inside of the cartridge 900 is divided into a plurality of sections to store different aromas in separate sections. An aroma that is frequently consumed may be stored in the plurality of sections.

(Discharge Unit 106)

The discharge unit 106 can discharge the aroma from the cartridge 900 housed in the cartridge housing unit 104 to outside. Specifically, the discharge unit 106 includes, for example, a microfan (not illustrated), and allows air to flow through an air flow path (not illustrated) provided in the cartridge 900 by the rotation of the microfan, thereby vaporizing and discharging the aroma inside the cartridge 900. In the present embodiment, the discharge unit 106 is not limited to the microfan, and may be, for example, an air pump, an air gun that compresses and pushes out air, a heater that vaporizes the aroma by heating, or the like.

(Control Unit 110)

Control unit 110 can integrally control the operation of the fragrance presentation device 100, and is realized by, for example, a processing circuit such as a central processing unit (CPU) or a graphics processing unit (GPU). Specifically, the control unit 110 can control the discharge unit 106 to synchronize the discharge of the aroma and the output of the content according to the aroma score.

Note that, in the present embodiment, the control unit 110 may finely adjust the timing to discharge indicated by the aroma score according to a delay in the output of the content, a delay in the discharge of the aroma, or the like. As a result, the discharge can be accurately synchronized with the output of the content.

Furthermore, in the present embodiment, for example, when the content is an electronic book and the trigger on the content designated by the aroma score is a page on the electronic book, the control unit 110 may perform control to discharge the designated aroma at a timing of detecting that an applicable page is displayed. Similarly, the control unit 110 may perform control to discharge the designated aroma at a timing of detecting the page that has been turned according to the trigger on the content specified by the aroma score. Furthermore, when the content is a game and input operation information from the user and biometric information or position information of the user can be detected, the control unit 110 may perform control to discharge the designated aroma at a timing of detecting the input operation or at a timing of detecting predetermined biometric information or position information.

(Content Acquisition Unit 112)

The content acquisition unit 112 can acquire the content data related to a moving image or the like via, for example, a communication unit (not illustrated) or a media interface (not illustrated) for reading a program or the like recorded in a predetermined recording medium (medium). Furthermore, the content acquisition unit 112 can output the content data acquired to the control unit 110. In addition, the content data may be stored in advance in the storage unit 114 described later. In this case, the storage unit 114 may be provided so as to be fixed inside the fragrance presentation device 100, or may be detachably provided in the fragrance presentation device 100.

In the present embodiment, the content data is not limited to a moving image (video) such as a movie, and may be an electronic book, a video game, a still image (photo, illustration, stamp, and the like), sound, music, or the like, may be tactile stimulus data used when a haptic stimulation is presented to the user by a haptics device, or may be a combination of these elements. Furthermore, in the present embodiment, the content data may include data for providing the user with temporally changing sound, image, or tactile stimulation, and is not particularly limited.

(Storage Unit 114)

The storage unit 114 stores programs, information, and the like for the control unit 110 to execute various types of processes, and information obtained by the processes. Furthermore, the storage unit 114 can store, for example, the above-described aroma score and content data. Note that the storage unit 114 is realized by, for example, a nonvolatile memory such as a flash memory or a storage device such as a hard disk drive (HDD).

(Display Unit 120)

The display unit 120 can display (output) a reproduced image (content) according to the control by the control unit 110. Specifically, the display unit 120 includes, for example, a liquid crystal display (LCD), an organic electro luminescence (EL) display, or the like, and can output the reproduced image included in the content data acquired by the content acquisition unit 112. In the present embodiment, the display unit 120 may be fixed inside the fragrance presentation device 100, or may be detachably provided in the fragrance presentation device 100.

(Sound Output Unit 122)

The sound output unit 122 can output the reproduced sound (content) according to the control by the control unit 110. Specifically, the sound output unit 122 includes, for example, a speaker, a headphone, or the like, and can output the reproduced sound included in the content data acquired by the content acquisition unit 112. The sound output unit 122 may be fixed inside the fragrance presentation device 100, or may be detachably provided in the fragrance presentation device 100.

<2.3 Processing Method>

Figure 7:
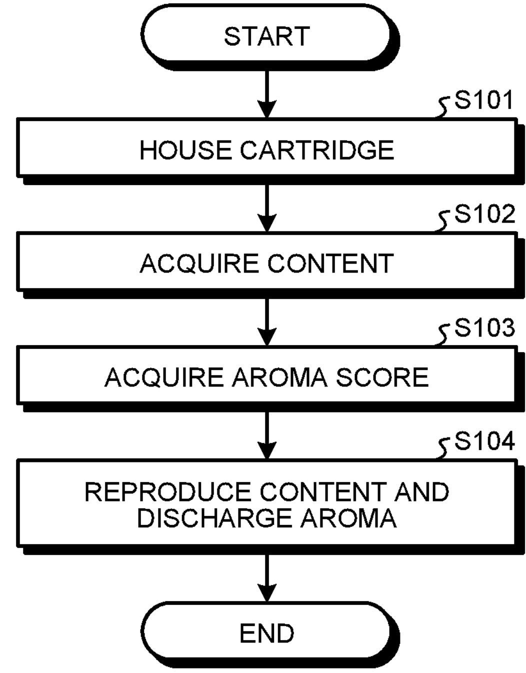
FIG. 7 is a flowchart illustrating an example of a processing method according to the first embodiment.

Next, a processing method according to the present embodiment will be described with reference to FIG. 7. FIG. 7 is a flowchart illustrating an example of the processing method according to the present embodiment. Specifically, as illustrated in FIG. 7, the processing method according to the present embodiment may include steps from Step S101 to Step S104. Details of these steps according to the present embodiment will be described below.

First, the cartridge 900 is housed in the fragrance presentation device 100 (Step S101). Next, the fragrance presentation device 100 acquires the content data (content) such as a moving image to be reproduced by download or the like via a communication unit (not illustrated) (Step S102). The fragrance presentation device 100 acquires the aroma score corresponding to the content acquired in Step S102 from the DB 704 through download or the like via the communication unit (not illustrated) (Step S103). Then, the fragrance presentation device 100 reproduces the content according to the content data and the aroma score acquired in Steps S102 and S103, and discharges the aroma in synchronization with the output of the content (Step S104).

As described above, in the present embodiment, the content data for reproducing the video or the like, the aroma score for presenting the fragrance to the user, and the cartridge 900 containing the aroma are separately provided to the user. In this way, according to the present embodiment, even in the case of existing content, the user can easily enjoy the fragrance together with the content at home or the like. Furthermore, in the present embodiment, since the existing content can be used without newly creating the content data in which the aroma score is integrated, an enormous pieces of content can be enjoyed as described above, and a broader range of entertainment can be provided to the user. As a result, the spread of this type of entertainment can be promoted.

3. Second Embodiment

Figure 8:
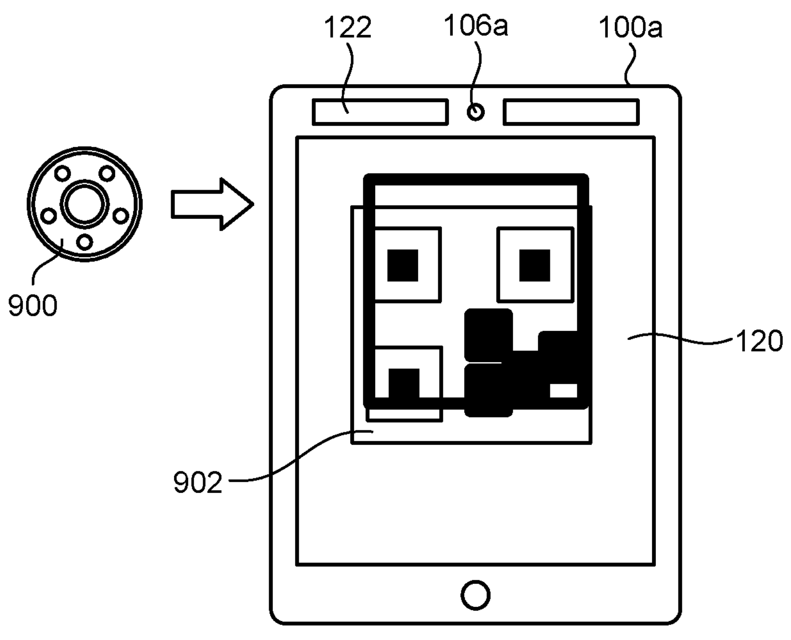
FIG. 8 is an explanatory diagram (part 1) illustrating a second embodiment of the present disclosure.
Figure 9:
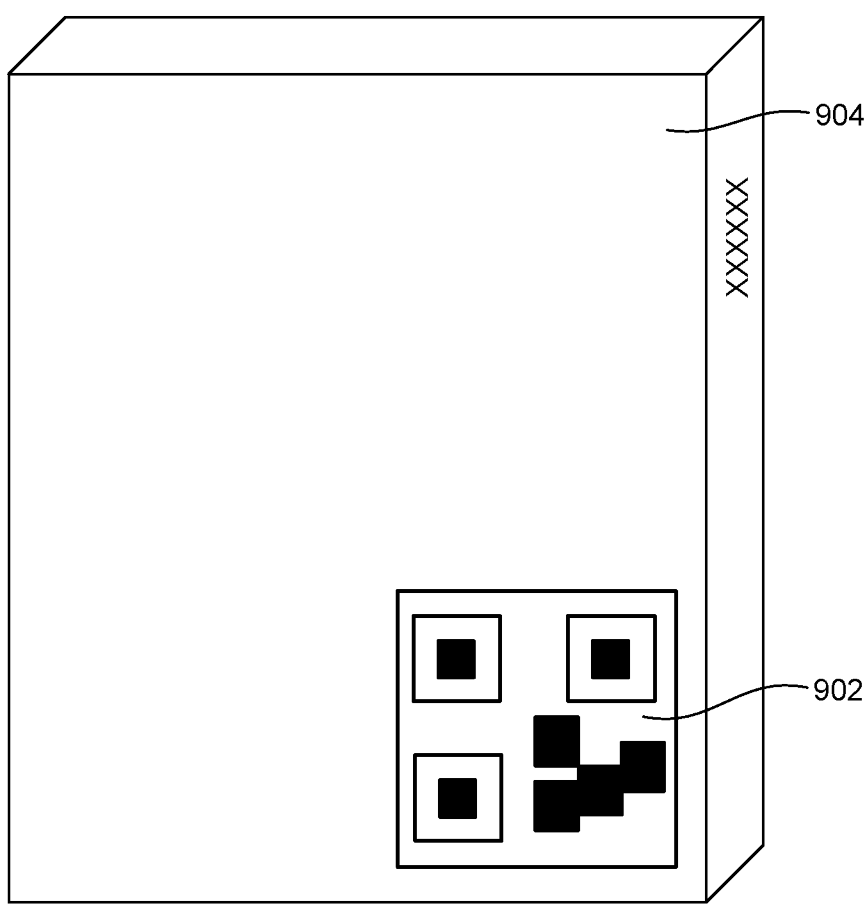
FIG. 9 is an explanatory diagram (part 2) illustrating the second embodiment.

In the first embodiment described above, the aroma score is acquired from the DB 704 through download or the like via the communication unit (not illustrated). In the second embodiment of the present disclosure described below, the aroma score is acquired by reading a one-dimensionally or two-dimensionally coded aroma score. In this way, according to the present embodiment, handling, processing, and the like of the aroma score can be facilitated, and convenience of the user can be improved. Hereinafter, details of the second embodiment will be described with reference to FIGS. 8 and 9. FIGS. 8 and 9 are explanatory diagrams illustrating the present embodiment.

In the present embodiment, for example, as illustrated in FIG. 8, the aroma score can be acquired by reading a one-dimensionally or two-dimensionally coded aroma score 902 by a reader 108 (see FIG. 10) provided on a rear surface side of a fragrance presentation device 100*a* according to the present embodiment. In the present embodiment, the coded aroma score 902 read in this way can be a one-dimensional code (e.g., barcode), a two-dimensional code (e.g., QR code (registered trademark) as illustrated in FIG. 8, or a code including a number, a character string, a pattern, or the like. Furthermore, in the present embodiment, the coded aroma score 902 may be a code indicating identification information of the aroma score itself or a code indicating identification information (e.g., serial number) of the content itself.

In the present embodiment, the coded aroma score 902 may be printed on a medium that stores the content data, a package 904 that stores the medium, or the like as illustrated in FIG. 9. Further, in the present embodiment, the coded aroma score 902 may be presented at a site on the Internet.

In the present embodiment, the coded aroma score is not limited to the form of the one-dimensional code or the two-dimensional code, and may be magnetic data or the like. The form is not particularly limited.

A configuration example of the fragrance presentation system 10 according to each embodiment of the present disclosure described below is common to the fragrance presentation system 10 according to the first embodiment. Therefore, the description of the configuration of the fragrance presentation system 10 according to the first embodiment and FIG. 4 used in the description can be referred to.

Accordingly, the description of the fragrance presentation system 10 according to the present embodiment is omitted below.

<3.1 Fragrance Presentation Device>

Figures 10, 11:
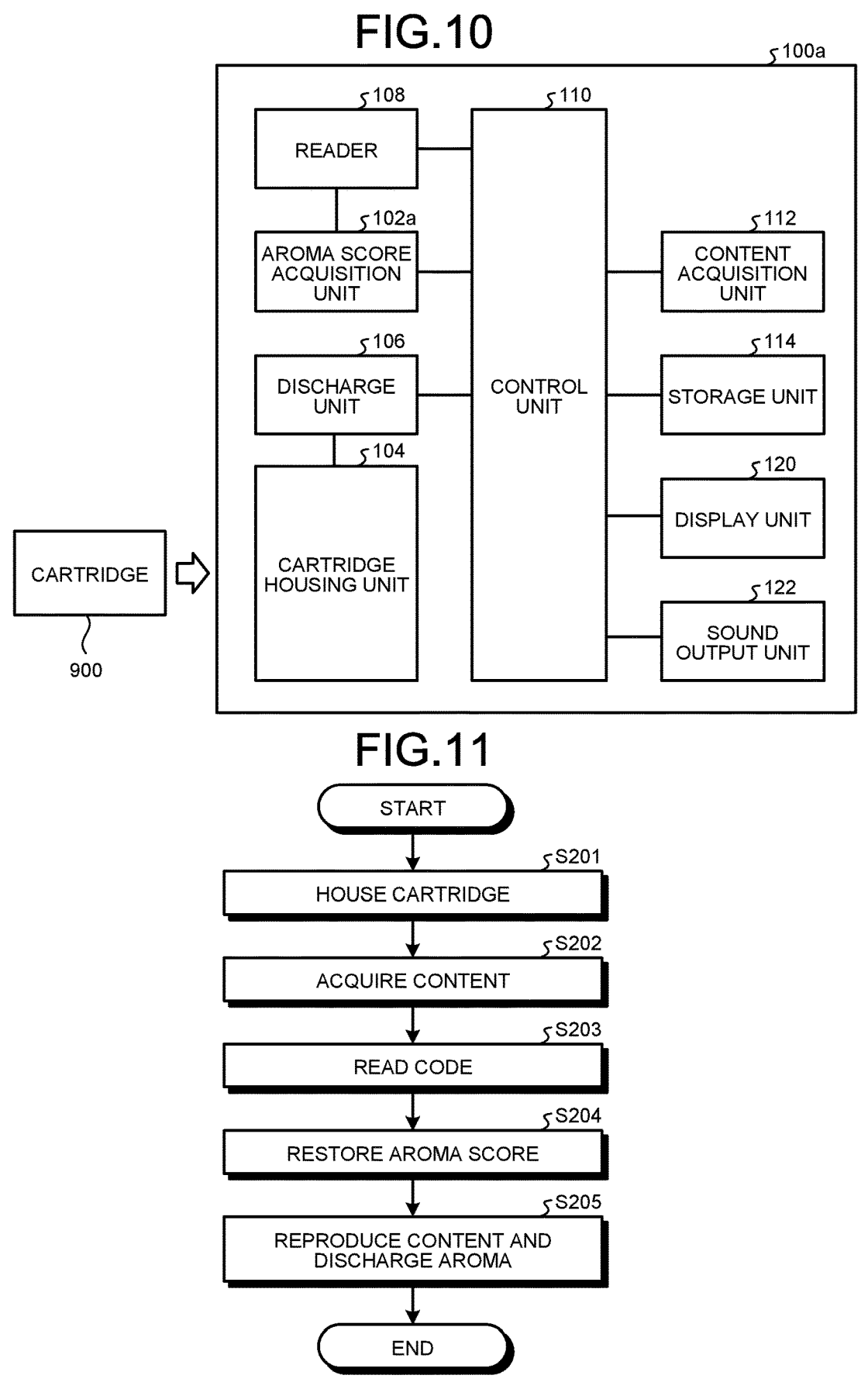

Next, a detailed configuration of the fragrance presentation device 100*a* according to the present embodiment will be described with reference to FIG. 10. FIG. 10 is an explanatory diagram illustrating a configuration example of functional blocks of the fragrance presentation device 100*a* according to the present embodiment. Specifically, as illustrated in FIG. 10, the fragrance presentation device 100*a* according to the present embodiment mainly includes an aroma score acquisition unit 102*a*, the cartridge housing unit 104, the discharge unit 106, the reader 108, the control unit 110, the content acquisition unit 112, the storage unit 114, the display unit 120, and the sound output unit 122. Hereinafter, the functional blocks of the fragrance presentation device 100*a* will be sequentially described. However, since the functional blocks other than the aroma score acquisition unit 102*a* and the reader 108 are common to the functional blocks of the fragrance presentation device 100 according to the first embodiment, the description of the functional blocks other than the aroma score acquisition unit 102*a* and the reader 108 will be omitted, and only the aroma score acquisition unit 102*a* and the reader 108 will be described.

(Aroma Score Acquisition Unit 102*a*)

The aroma score acquisition unit 102*a* analyzes an image of the coded aroma score 902 read by the reader 108 described later to acquire the aroma score (restoration of the aroma score). In the present embodiment, when the code read by the reader 108 described later is the aroma score or information corresponding to the identification information of the content, the aroma score is acquired by download or the like based on the identification information obtained by analyzing an image of the code that has been read.

(Reader 108)

The reader 108 can read the one-dimensionally or two-dimensionally coded aroma score 902 and output the aroma score to the aroma score acquisition unit 102*a*. Specifically, for example, the reader 108 acquires an image of the coded aroma score 902 by forming the image on an imaging element such as a charge coupled device (CCD) or a complementary metal oxide semiconductor (CMOS) through a lens.

<3.2 Processing Method>

Next, a processing method according to the present embodiment will be described with reference to FIG. 11. FIG. 11 is a flowchart illustrating an example of the processing method according to the present embodiment. Specifically, as illustrated in FIG. 11, the processing method according to the present embodiment may include steps from Step S201 to Step S205. Details of these steps according to the present embodiment will be described below. In the following description, only differences from the above-described first embodiment will be described, and the description of common points with the first embodiment will be omitted.

Since Steps S201 and S202 are similar to Steps S101 and S102 of the first embodiment illustrated in FIG. 7, the description thereof is omitted here.

The fragrance presentation device 100*a* reads the one-dimensionally or two-dimensionally coded aroma score 902 (Step S203). Next, the fragrance presentation device 100*a* analyzes the image of the coded aroma score 902 to acquire the aroma score (restoration of the aroma score) (Step S204).

Since Step S205 is similar to Step S104 of the first embodiment illustrated in FIG. 7, the description thereof is omitted here.

As described above, in the present embodiment, the aroma score is acquired by reading the one-dimensionally or two-dimensionally coded aroma score. In this way, according to the present embodiment, handling, processing, and the like of the aroma score can be facilitated, and convenience of the user can be improved.

4. Third Embodiment

Figure 12:
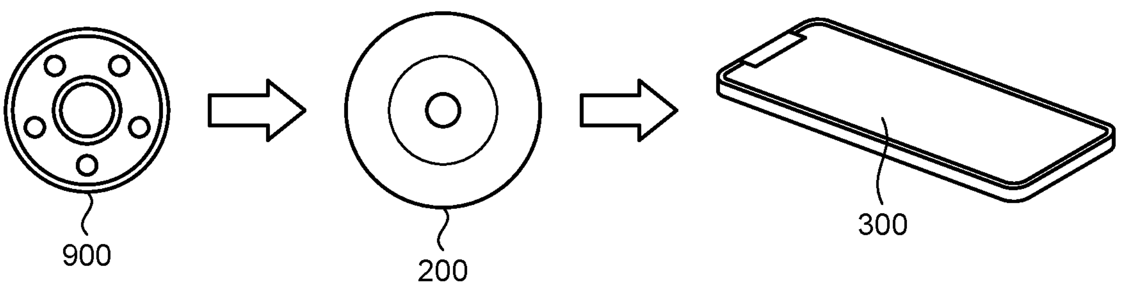
FIG. 12 is an explanatory diagram illustrating a third embodiment of the present disclosure.

In the first embodiment described above, the fragrance presentation device 100 is an integrated device capable of discharging the aroma and outputting the content by the same device, but the present disclosure is not limited to the use of the device in this form. In a third embodiment of the present disclosure described below, separate devices are used for discharging the aroma and outputting the content. Hereinafter, details of the third embodiment will be described with reference to FIG. 12. FIG. 12 is an explanatory diagram illustrating the present embodiment.

Specifically, as illustrated in FIG. 12, in the present embodiment, the aroma is discharged by a fragrance presentation device 200, and the content is output by an information processing terminal 300. In other words, in the present embodiment, the function of the fragrance presentation device 100 according to the first embodiment can be realized by cooperation of the fragrance presentation device 200 and the information processing terminal 300.

Specifically, the information processing terminal 300 can be a device such as a smartphone, a mobile phone, a tablet personal computer (PC), a laptop PC, a notebook PC, a game machine, a media player, a music player, a speaker, a television, a projector, an in-vehicle audio visual (AV) device, or a head mounted display (HMD). In addition, in the fragrance presentation device 200 according to the present embodiment, the cartridge 900 containing one or a plurality of aromas is detachably housed, and the aromas in the cartridge 900 can be discharged.

In the following description, it is assumed that the fragrance presentation device 200 can be physically attached to the information processing terminal 300, but the present embodiment is not limited thereto. For example, in the present embodiment, the fragrance presentation device 200 and the information processing terminal 300 may be connected to each other through a common interface (I/F) so as to be able to input and output information, and may be used in a physically separated state. In other words, in the present embodiment, the fragrance presentation device 200 and the information processing terminal 300 may be connected to each other via a network for various wired or wireless communications or the like.

<4.1 Fragrance Presentation Device>

Figure 13:
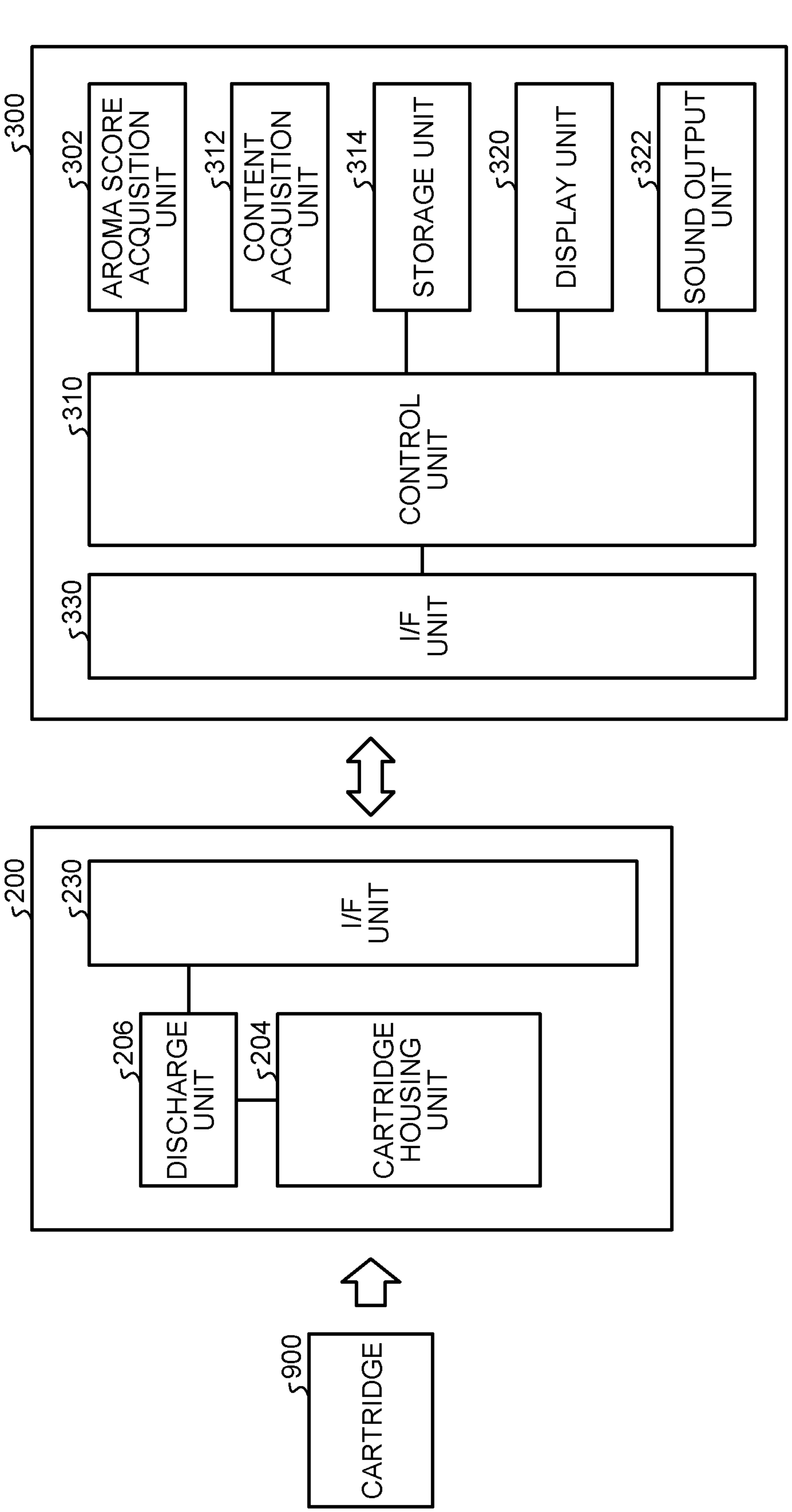
FIG. 13 is an explanatory diagram illustrating a configuration example of functional blocks of a fragrance presentation device 200 and an information processing terminal 300 according to the third embodiment.

Next, a detailed configuration of the fragrance presentation device 200 according to the present embodiment will be described with reference to FIG. 13. FIG. 13 is an explanatory diagram illustrating a configuration example of functional blocks of the fragrance presentation device 200 and the information processing terminal 300 according to the present embodiment. Specifically, as illustrated in FIG. 13, the fragrance presentation device 200 according to the present embodiment mainly includes a cartridge housing unit 204, a discharge unit 206, and an interface (I/F) unit 230. Hereinafter, each functional block of the fragrance presentation device 200 will be sequentially described.

(Cartridge Housing Unit 204)

Similarly to the cartridge housing unit 104 according to the first embodiment, the cartridge housing unit 204 can detachably house the cartridge 900.

(Discharge Unit 206)

Similarly to the discharge unit 106 according to the first embodiment, the discharge unit 206 can discharge the aroma from the cartridge 900 housed in the cartridge housing unit 204 to the outside. Furthermore, in the present embodiment, the discharge unit 206 is controlled by the information processing terminal 300 to be described later.

(I/F Unit 230)

The I/F unit 230 is a connection unit for connecting to the information processing terminal 300, and is realized by, for example, a universal serial bus (USB) connector, and can input and output information to and from the information processing terminal 300.

<4.2 Information Processing Terminal>

Next, a detailed configuration of the information processing terminal 300 according to the present embodiment will be described with reference to FIG. 13. Specifically, as illustrated in FIG. 13, the information processing terminal 300 according to the present embodiment mainly includes an aroma score acquisition unit 302, a control unit 310, a content acquisition unit 312, a storage unit 314, a display unit 320, a sound output unit 322, and an I/F unit 330. Hereinafter, each functional block of the fragrance presentation device 200 will be sequentially described.

(Aroma Score Acquisition Unit 302)

Similarly to the aroma score acquisition unit 102 according to the first embodiment, the aroma score acquisition unit 302 acquires the aroma score associated with identification information of the content from, for example, the DB 704 stored in the server 700 to be described later.

(Control Unit 310)

Similarly to the control unit 110 according to the first embodiment, the control unit 310 can integrally control the operation of the information processing terminal 300, and can further control the operation of the fragrance presentation device 200. Specifically, the control unit 310 can control the fragrance presentation device 200 to synchronize the discharge of the aroma with the output of the content according to the aroma score.

(Content Acquisition Unit 312)

Similarly to the content acquisition unit 112 according to the first embodiment, the content acquisition unit 312 can acquire the content data via, for example, the communication unit (not illustrated) or the media interface (not illustrated).

(Storage Unit 314)

Similarly to the storage unit 114 according to the first embodiment, the storage unit 314 stores programs, information, and the like for the control unit 310 to execute various types of processes, and store information obtained through the processes.

(Display Unit 320)

Similarly to the display unit 120 according to the first embodiment, the display unit 320 can display a reproduced image according to the control by the control unit 310.

(Sound Output Unit 322)

Similarly to the sound output unit 122 according to the first embodiment, the sound output unit 322 can output reproduced sound according to the control by the control unit 310.

(I/F Unit 330)

The I/F unit 330 is a connection unit for connecting to the fragrance presentation device 200, and is realized by, for example, a USB connector, and can input and output information to and from the fragrance presentation device 200.

<4.3 Processing Method>

Figure 14:
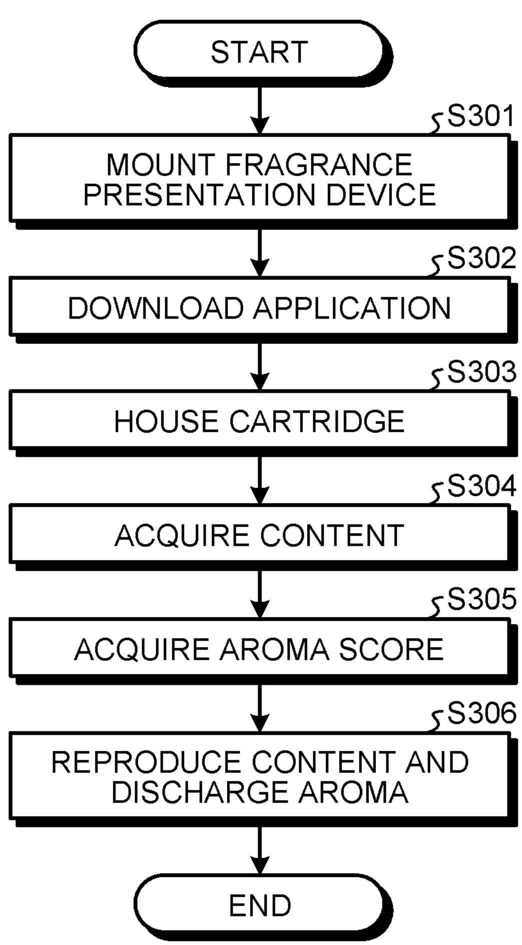
FIG. 14 is a flowchart illustrating an example of a processing method according to the third embodiment.

Next, the processing method according to the present embodiment will be described with reference to FIG. 14. FIG. 14 is a flowchart illustrating an example of the processing method according to the present embodiment. Specifically, as illustrated in FIG. 11, the processing method according to the present embodiment may include steps from Step S301 to Step S306. Details of these steps according to the present embodiment will be described below. In the following description, only differences from the above-described first embodiment will be described, and the description of common points with the first embodiment will be omitted.

First, the fragrance presentation device 200 is mounted on the information processing terminal 300 (Step S301). Next, an application for presenting the fragrance to the user together with the content is downloaded to the information processing terminal 300 (Step S302).

Since Steps S303 to S306 are similar to Steps S101 to S104 illustrated in FIG. 7, the description thereof is omitted here.

As described above, according to the present embodiment, the entertainment including the fragrance together with the content can be presented to the user by cooperation of the fragrance presentation device 200 that discharges the aroma and the information processing terminal 300 that outputs the content.

<4.4 Modification>

Figure 15:
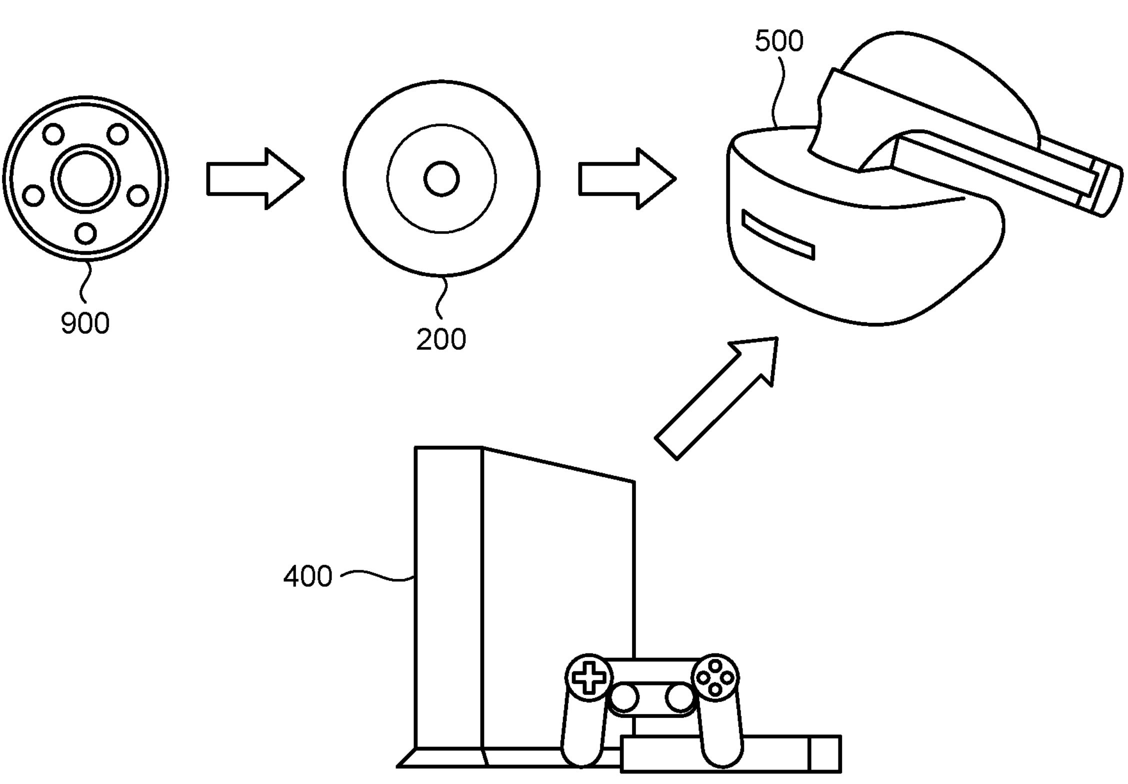
FIG. 15 is an explanatory diagram illustrating a modification of the third embodiment.

The present embodiment can also be applied to the game machine 400 and the HMD 500. Hereinafter, a modification of the present embodiment will be described with reference to FIGS. 15 and 16. FIG. 15 is an explanatory diagram illustrating the modification of the present embodiment, and FIG. 16 is an explanatory diagram illustrating a configuration example of functional blocks of the fragrance presentation device 200, the game machine 400, and the HMD 500 according to the modification of the present embodiment.

Specifically, as illustrated in FIG. 15, in the present modification, the game machine 400 and the HMD 500 can be used instead of the information processing terminal 300. For example, the game machine 400 may cooperate with the HMD 500 to provide a video game to the user. Furthermore, the HMD 500 is, for example, a display device that can be worn on the head of the user, and can display a moving image or the like according to the control by the game machine 400 described above.

More specifically, as illustrated in FIG. 16, similarly to the information processing terminal 300, the game machine 400 according to the present modification mainly includes an aroma score acquisition unit 402, a control unit 410, a content acquisition unit 412, a storage unit 414, and an I/F unit 430. Furthermore, as illustrated in FIG. 16, similarly to the information processing terminal 300, the HMD 500 according to the present modification mainly includes a control unit 510, a display unit 520, a sound output unit 522, and an I/F unit 530. Note that, in the present modification, the display unit 520 of the HMD 500 may be a video see-through type, a see-through type, or a retinal projection type, and is not particularly limited. Furthermore, in the present modification, the HMD 500 may be a haptics device that presents a tactile stimulation to the user.

5. Fourth Embodiment

Figure 17:
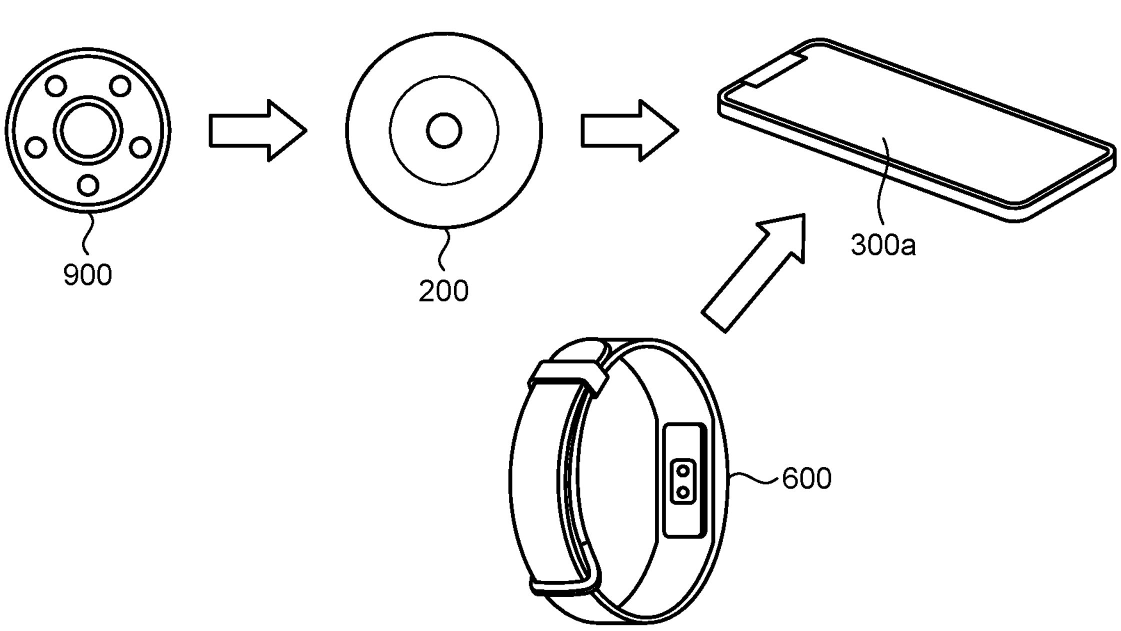
FIG. 17 is an explanatory diagram illustrating a fourth embodiment of the present disclosure.

How the user feel aroma changes according to a physical condition of the user. Therefore, in a fourth embodiment of the present disclosure described below, how the aroma is discharged is changed according to the physical condition of the user. In the present embodiment, for example, when the user is in an excited state, a smaller amount of an exciting aromatic element is discharged. Furthermore, in the present embodiment, for example, when the user has a blocked nose, a large amount of aroma may be discharged so that the user can catch aroma, or conversely, the discharge of the aroma may be stopped. In this way, according to the present embodiment, since the fragrance can be presented according to the physical condition of the user, the user's satisfaction with the content can be further enhanced. Hereinafter, the fourth embodiment of the present disclosure will be described with reference to FIG. 17. FIG. 17 is an explanatory diagram illustrating the present embodiment.

Specifically, as illustrated in FIG. 17, the present embodiment employs a biological information sensor (biological information acquisition unit) 600 capable of acquiring biological information of the user. For example, the biological information sensor 600 can be a wearable device that can be worn on a part of the user's body (earlobe, neck, arm, wrist, ankle, etc.) or an implant device (implant terminal) inserted into the user's body. More specifically, the wearable device can be a wearable device of various types such as an HMD type, an eyeglass type, an ear device type, an anklet type, a bracelet (wristband) type (example in FIG. 17), a collar type, an eyewear type, a pad type, a batch type, and a clothing type. Note that details of the biological information sensor 600 will be described later.

<5.1 Information Processing Terminal>

Figure 18:
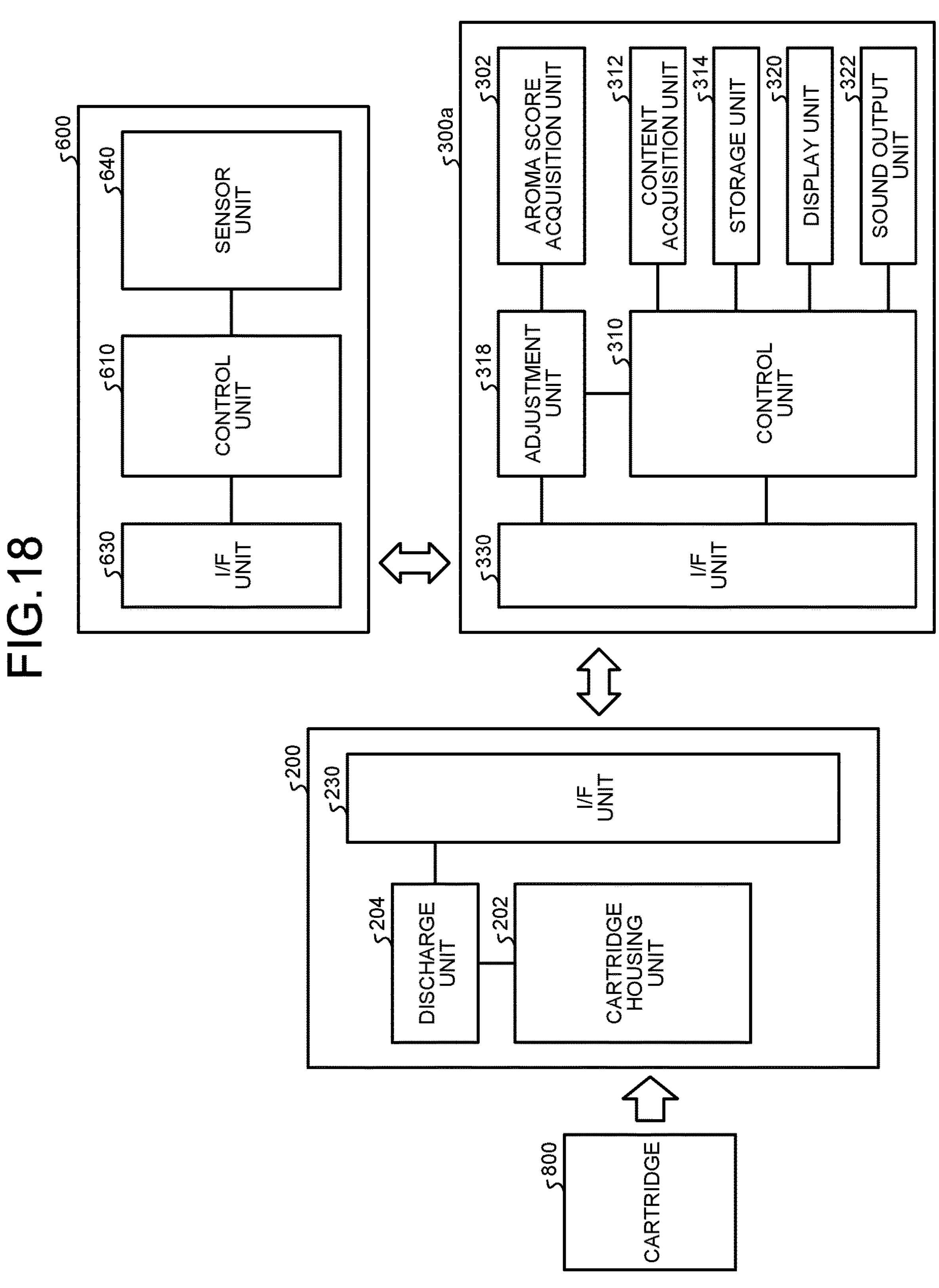
FIG. 18 is an explanatory diagram illustrating a configuration example of functional blocks of the fragrance presentation device 200, an information processing terminal 300*a*, and a biological information sensor 600 according to the fourth embodiment.

First, a detailed configuration of an information processing terminal 300*a* according to the present embodiment will be described with reference to FIG. 18. FIG. 18 is an explanatory diagram illustrating a configuration example of functional blocks of the fragrance presentation device 200, the information processing terminal 300*a*, and the biological information sensor 600 according to the present embodiment. Specifically, as illustrated in FIG. 18, the information processing terminal 300*a* according to the present embodiment mainly includes the aroma score acquisition unit 302, the control unit 310, the content acquisition unit 312, the storage unit 314, an adjustment unit 318, the display unit 320, the sound output unit 322, and the I/F unit 330. Hereinafter, each functional block of the information processing terminal 300*a* will be sequentially described. However, since components other than the adjustment unit 318 are common to those of the information processing terminal 300 according to the third embodiment, the description of the components other than the adjustment unit 318 is omitted, and only the adjustment unit 318 will be described.

(Adjustment Unit 318)

The adjustment unit 318 acquires sensing data from the biological information sensor 600 to be described later, adjusts the aroma score acquired by the aroma score acquisition unit 302 according to the biological information obtained by analyzing the sensing data, and outputs the aroma score to the control unit 310. The control unit 310 further controls the fragrance presentation device 200 according to the aroma score adjusted. For example, when it is recognized that the user is excited by a pulse wave or the like, the adjustment unit 318 adjusts the aroma score so as to discharge less exciting aroma. Furthermore, for example, when a sniffling sound is detected from the user, the adjustment unit 318 considers that the user's nose is blocked and adjusts the aroma score to discharge a large amount of aroma so that the user can catch the aroma. In addition, for example, instead of discharging the large amount of aroma, the aroma score may be adjusted to discharge a stronger aroma in the same aromatic system. Furthermore, an aroma type may be selected in accordance with the state of the user based on the biological information. Note that the adjustment unit 318 is realized by, for example, a processing circuit such as a CPU.

<5.2 Biological Information Sensor>

Next, a detailed configuration of the biological information sensor 600 according to the present embodiment will be described with reference to FIG. 18. As illustrated in FIG. 18, the biological information sensor 600 according to the present embodiment mainly includes the control unit 310, the I/F unit 330, and a sensor unit 640. Hereinafter, each functional block of the biological information sensor 600 will be sequentially described.

(Control Unit 610)

A control unit 610 can integrally control the operation of the biological information sensor 600, and is realized by, for example, a processing circuit such as a CPU.

(I/F Unit 630)

An I/F unit 630 is a connection unit for connecting to the information processing terminal 300*a*, and is realized by, for example, a USB connector, and can input and output information to and from the information processing terminal 300*a*.

(Sensor Unit 640)

The sensor unit 640 is a sensor that detects the biological information of the user, and can be, for example, various sensors that are directly attached to a part of the user's body and measure the user's heartbeat, pulse, blood pressure, brain waves, respiration, sweating, myoelectric potential, skin temperature, skin electrical resistance, and the like. Furthermore, the sensor unit 640 may include an imaging device, and in this case, the imaging device may acquire sensing data regarding the pulse of the user, the movement (expression) of the muscles of expression, the movement of the line of sight, and the like. Furthermore, the sensor unit 640 may be a sound sensor, and may detect a spoken voice of the user or a sound due to a motion of the user. Then, the sensing data acquired by the sensor unit 640 is output by the information processing terminal 300*a* via the I/F unit 630 described above.

In the present embodiment, the fragrance presentation device 200 is similar to that of the above-described third embodiment, and thus the description thereof is omitted here.

<5.3 Processing Method>

Figure 19:
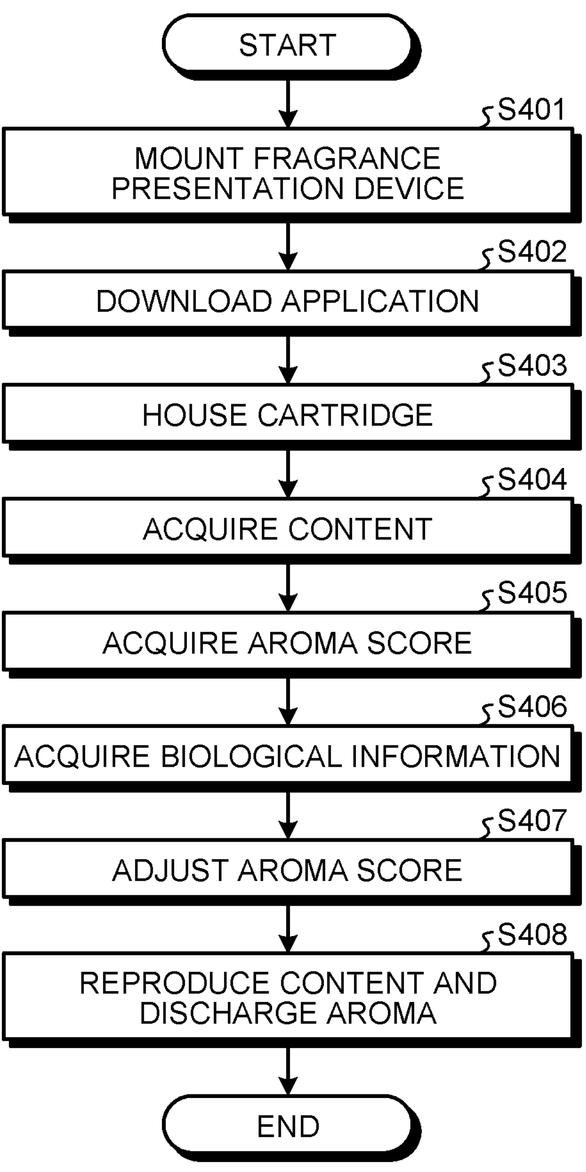
FIG. 19 is a flowchart illustrating an example of a processing method according to the fourth embodiment.

Next, a processing method according to the present embodiment will be described with reference to FIG. 19. FIG. 19 is a flowchart illustrating an example of the processing method according to the present embodiment. Specifically, as illustrated in FIG. 19, the processing method according to the present embodiment may include steps from Step S401 to Step S408. Details of these steps according to the present embodiment will be described below. In the following description, only differences from the above-described third embodiment will be described, and the description of common points with the third embodiment will be omitted.

Since Steps S401 to S405 are similar to Steps S301 to S305 of the third embodiment illustrated in FIG. 14, the description thereof is omitted here.

Next, the biological information sensor 600 acquires the sensing data related to the biological information of the user (Step S406). Next, the information processing terminal 300*a* analyzes the sensing data, and adjusts the aroma score acquired in Step S405 according to the biological information of the user obtained by the analysis (Step S407).

Step S408 is similar to Step S306 of the third embodiment illustrated in FIG. 7, and thus the description thereof is omitted here.

As described above, according to the present embodiment, since the form of discharging the aroma can be changed according to the physical condition of the user, the user's satisfaction with the content can be further enhanced.

<5.4 Modification>

In the above-described embodiment, the biological information sensor 600 is used, but in the present embodiment, a surrounding environment sensor (not illustrated) may be used instead of the biological information sensor 600 or together with the biological information sensor 600. For example, the surrounding environment sensor is a sensor that detects a state of the surrounding environment of the user, and specifically, can be various sensors that detect a temperature, humidity, air volume, weather, and the like of the surrounding environment of the user.

Then, the adjustment unit 318 acquires the sensing data from an surrounding environment sensor (not illustrated), adjusts the aroma score acquired by the aroma score acquisition unit 302 according to the environment information obtained by analyzing the sensing data, and outputs the aroma score adjusted to the control unit 310. The control unit 310 further controls the fragrance presentation device 200 according to the aroma score adjusted. For example, since the form of spreading the aroma changes according to the temperature, humidity, and the like, the adjustment unit 318 adjusts the aroma score so as to change the aroma discharge amount in consideration of the temperature, humidity, and the like of the surrounding environment.

Furthermore, in the present modification, the surrounding environment sensor (not illustrated) may include a position sensor that detects the position of the user and the positions of people around the user. Specifically, the position sensor may be a global navigation satellite system (GNSS) receiver or the like. In this case, the position sensor acquires sensing data indicating latitude/longitude information of a current location of the user based on a signal from a GNSS satellite. Furthermore, in the present modification, since it is possible to detect a relative positional relationship of the user from, for example, radio frequency identification (RFID), Wi-Fi access point, or information of a radio base station, these communication devices may be used as a position sensor.

Then, the adjustment unit 318 acquires the sensing data from the position sensor (not illustrated), adjusts the aroma score acquired by the aroma score acquisition unit 302 according to the position information obtained by analyzing the sensing data, and outputs the aroma score adjusted to the control unit 310. The control unit 310 further controls the fragrance presentation device 200 according to the aroma score adjusted. For example, the adjustment unit 318 adjusts the aroma score so as to change how the aroma spreads according to a place where the user is located. Specifically, when the user is in an office, the aroma score is adjusted to discharge less aroma so that nearby people do not feel uncomfortable due to the fragrance. Furthermore, when the user exists at a position close to another person, similar adjustment may be performed. In addition, when the user is at home or in a large room, the aroma score may be adjusted to discharge a stronger aroma so that the fragrance securely reaches the user. In addition, for example, instead of discharging the large amount of aroma, the aroma score may be adjusted to discharge a stronger aroma in the same aromatic system. Furthermore, the aroma type may be selected in accordance with the state of the user based on the environment information.

As described above, according to the present modification, since the form of discharging the aroma can be changed according to the environment around the user, it is possible to increase the user's satisfaction with the content and to avoid giving discomfort to a person around the user due to the fragrance.

6. Fifth Embodiment

Figure 20:
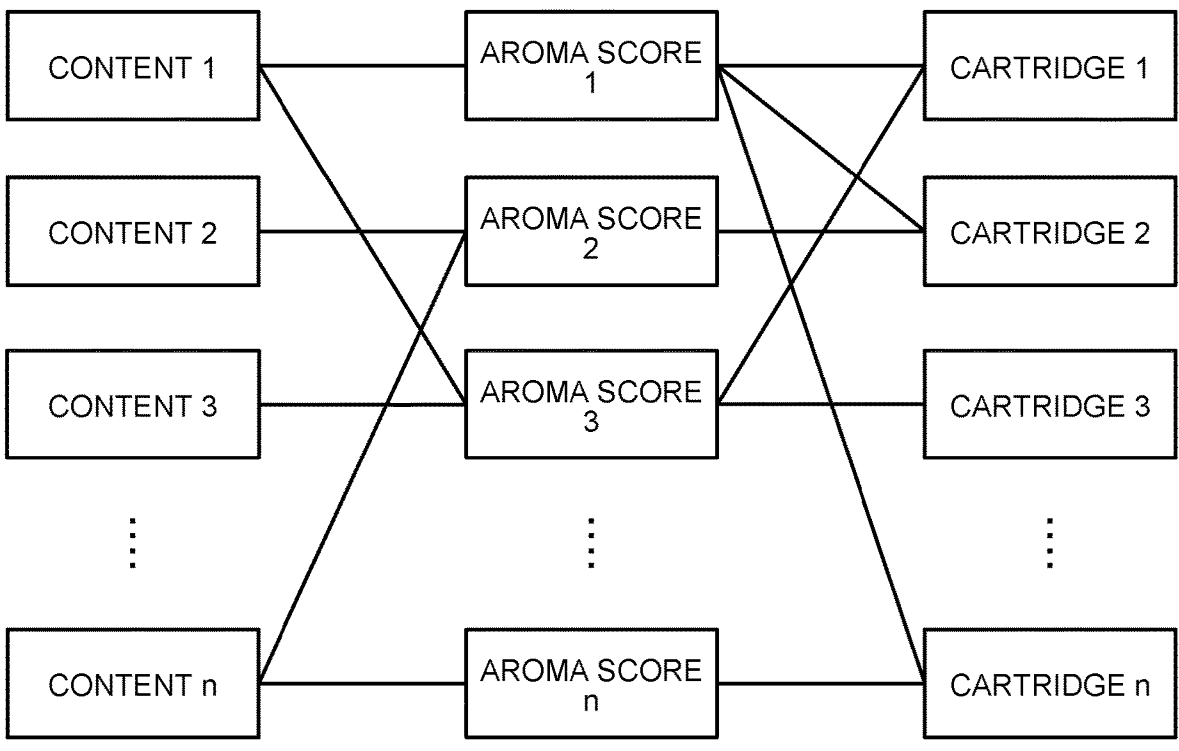
FIG. 20 is an explanatory diagram illustrating a fifth embodiment of the present disclosure.

A fifth embodiment of the present disclosure, which is an embodiment related to the server 700 described above, will be described with reference to FIG. 20. FIG. 20 is an explanatory diagram illustrating the present embodiment. In the present embodiment, the above-described aroma score is managed by the server 700. As illustrated in FIG. 20, in the server 700, each aroma score is stored as data separate from the content data, but is managed in association with the corresponding content or the cartridge 900. More specifically, each aroma score is stored in the server 700 in association with the identification information (e.g., management number or the like) of the corresponding content and the identification information (e.g., management number or the like) of the corresponding cartridge 900. In the present embodiment, as described above, the content data, the aroma score, and the cartridge 900 can be separately provided to the user by managing the aroma score in association with the content and the cartridge 900. In this way, according to the present embodiment, even in the case of existing content, the user can easily enjoy the fragrance corresponding to the content together with the content at home or the like. Furthermore, in the present embodiment, the aroma score can also be used as a label indicating a feature of each content.

As illustrated in FIG. 20, each aroma score is not limited to one-to-one correspondence with the content and the cartridge 900. For example, in the present embodiment, each aroma score may correspond to a plurality of cartridges 900. Further, for example, in the present embodiment, each aroma score may correspond to a plurality of pieces of content.

<6.1 Server>

Figure 21:
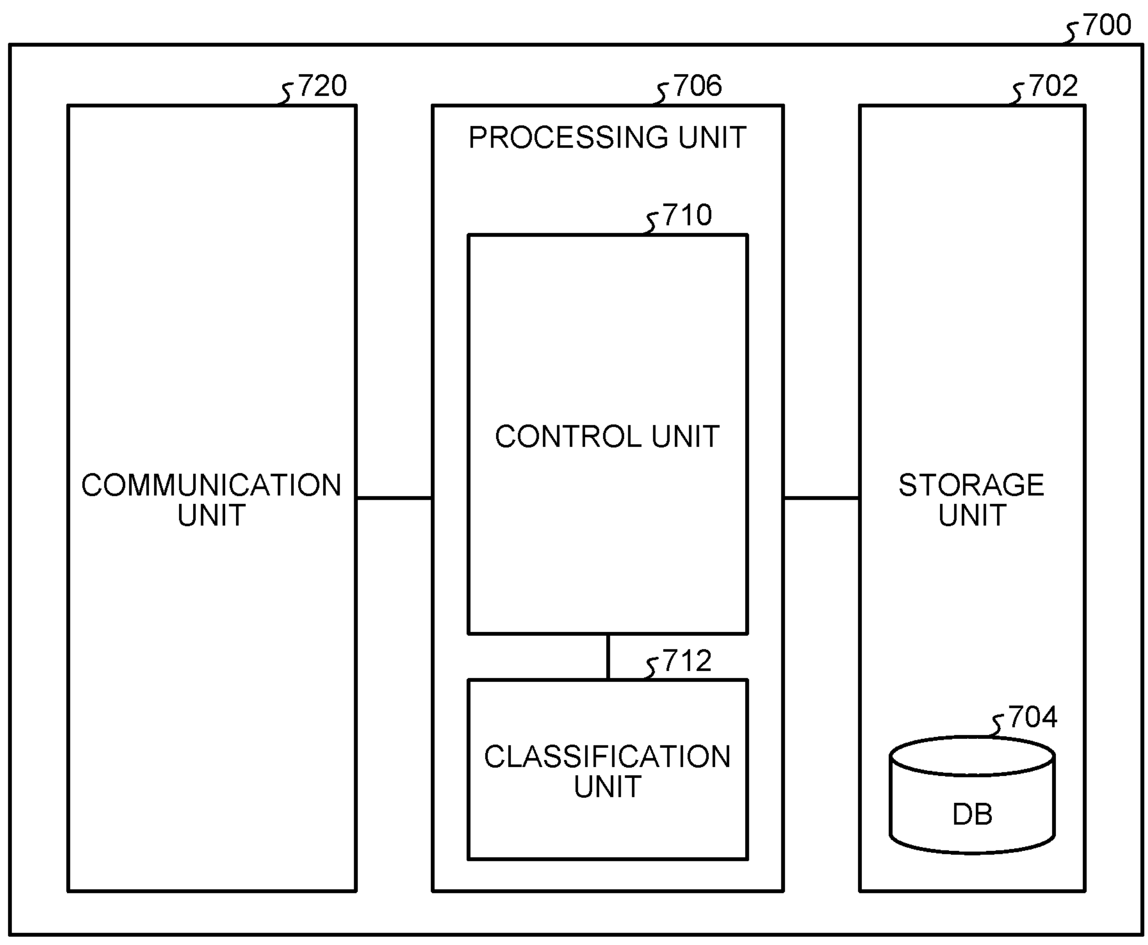
FIG. 21 is an explanatory diagram illustrating a configuration example of functional blocks of a server 700 according to the fifth embodiment.

First, a detailed configuration of the server 700 according to the present embodiment will be described with reference to FIG. 21. FIG. 21 is an explanatory diagram illustrating a configuration example of functional blocks of the server 700 according to the present embodiment. As illustrated in FIG. 21, the server 700 according to the present embodiment mainly includes the control unit 310, a storage unit 702, a processing unit 706, and a communication unit (distribution unit) 720. Hereinafter, each functional block of the server 700 will be sequentially described.

(Storage Unit 702)

The storage unit 702 stores, for example, the aroma score including a variable-length data array including a plurality of characters or numbers in association with the identification information of the content and the identification information of the cartridge as a DB 70. Note that the storage unit 702 is realized by, for example, a storage device such as an HDD.

(Processing Unit 706)

The processing unit 706 can integrally control the operation of the server 700, and is realized by, for example, a processing circuit such as a CPU. Specifically, the processing unit 706 includes a control unit 710 that integrally controls the operation of the server 700, a classification unit 712 that classifies pieces of content using the aroma score as a label indicating a feature of each content, and the like. Note that details of the classification unit 712 will be described later.

(Communication Unit 720)

The communication unit 720 can transmit and receive information to and from an external device such as the fragrance presentation device 100, and for example, can distribute the one-dimensionally or two-dimensionally coded aroma score in association with the identification information of the content. In other words, the communication unit 720 can be a communication interface having a function of transmitting and receiving data. In the present embodiment, the communication unit 720 is realized by, for example, a communication device such as a communication antenna, a transmission/reception circuit, or a port.

<6.2 Classification Unit>

Figure 22:
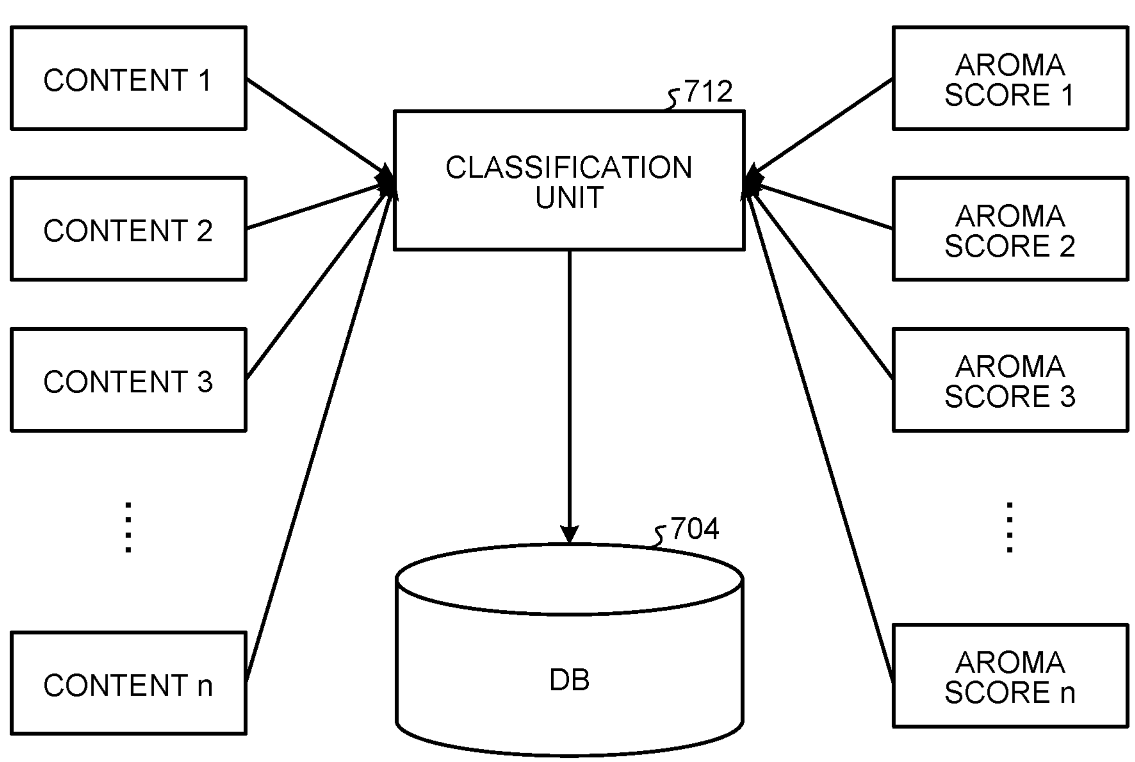
FIG. 22 is an explanatory diagram (part 1) illustrating a classification unit 712 according to the fifth embodiment.
Figure 23:
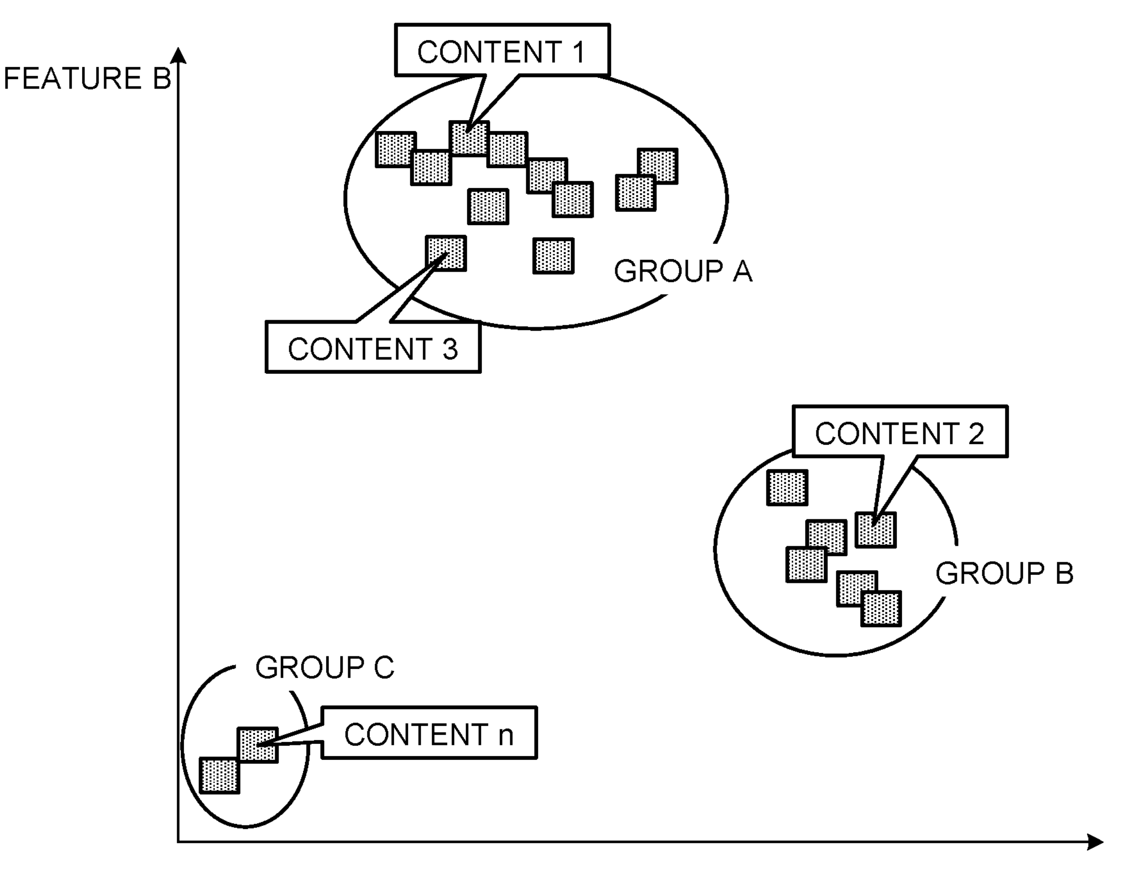
FIG. 23 is an explanatory diagram (part 2) illustrating the classification unit 712 according to the fifth embodiment.

Next, the classification unit 712 according to the present embodiment will be described with reference to FIGS. 22 and 23. FIGS. 22 and 23 are explanatory diagrams illustrating the classification unit 712 according to the present embodiment. In the present embodiment, as illustrated in FIG. 22, the classification unit 712 classifies each content by using the aroma score associated with each content as a label indicating a feature of each content. In other words, the classification unit 712 is a classifier that classifies the content according to each aroma score, and for example, a classification result obtained in this manner may be included in the DB 704 described above.

Specifically, in the present embodiment, for example, as illustrated in FIG. 23, the classification unit 712 can classify pieces of content into clusters (groups A to C) by extracting features of a predetermined type (e.g., a discharge amount of a predetermined aroma A and a discharge amount of a predetermined aroma B) from the aroma score associated with each content and determining whether the extracted features are similar.

Furthermore, in the present embodiment, the feature point and the feature amount of the aroma score in each cluster may be extracted using machine learning by a recurrent neural network or the like to generate a classification database in advance (e.g., supervised learning, semi-supervised learning, and unsupervised learning). The classification database generated here can be used for classification by the classification unit 712.

Note that the classification result of the content can be used as, for example, data for selecting recommended content when the content is recommended to the user. For example, by referring to the classification result of the content, content having the aroma score similar to the content viewed by the user can be recommended as content to be viewed next by the user.

In addition, it is considered that there is a high possibility that the cartridge 900 can be shared between pieces of content having similar aroma scores. Therefore, by referring to the classification result of the content, it is also possible to search for the cartridge 900 that can be shared or search for content that allows the user to continue to use the cartridge 900 that is currently used.

As described above, according to the present embodiment, by managing the aroma score in association with the content or the cartridge 900 by the server 700, the content data, the aroma score, and the cartridge 900 can be separately provided to the user. In this way, according to the present embodiment, even in the case of existing content, the user can easily enjoy the fragrance corresponding to the content together with the content.

Furthermore, in the present embodiment, by classifying each content by using the above-described aroma score as the label indicating the feature of each content, it is possible to recommend, to the user, appropriate content or introduce content capable of sharing the cartridge 900.

7. Sixth Embodiment

A sixth embodiment of the present disclosure, which is an embodiment related to the generator 800 described above, will be described with reference to FIG. 24. FIG. 24 is an explanatory diagram illustrating a sub-aroma score according to the present embodiment.

In the present embodiment, for example, when meta-information given to the content data, such as a title of the existing content or information introducing the content, includes information such as a "seaside scenery" or "sea", the aroma score corresponding to the content is generated using a sub-aroma prepared in advance with aroma of the "seaside" as illustrated in FIG. 24. Furthermore, in the present embodiment, for example, when the meta information includes information on a "flower field" next to the "sea", the aroma score corresponding to the content may be generated using the sub-aroma score prepared in advance with the aroma of the seaside and a sub-aroma score with aroma of the flower field. In this case, in the present embodiment, the aroma score is generated such that the aroma is discharged according to the sub-aroma score for the aroma of the "seaside" at the timing when the "sea" appears in the content, and the aroma is discharged according to the sub-aroma score for the aroma of the "flower field" at the timing when the "flower field" appears in the content. In this way, according to the present embodiment, the aroma score corresponding to the existing content can be easily generated.

Furthermore, in the present embodiment, for example, when the meta information includes information on a person or the like (artist or character (personified icon)) appearing in the content, the aroma score corresponding to the content may be generated using the sub-aroma score prepared in advance with aroma corresponding to the person or character.

<7.1 Generator>

Figure 25:
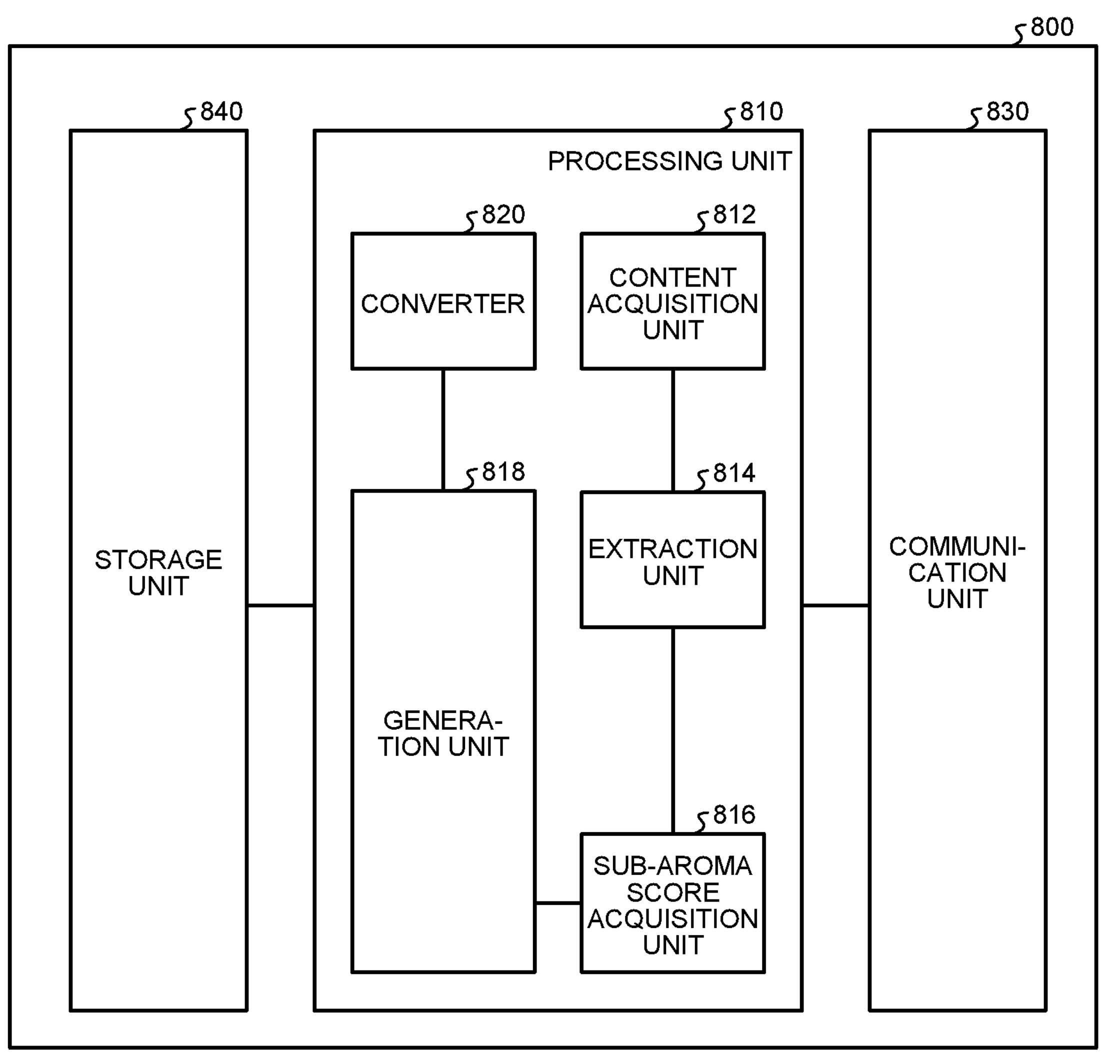
FIG. 25 is an explanatory diagram illustrating a configuration example of functional blocks of a generator 800 according to the sixth embodiment.

First, a detailed configuration of the generator 800 that generates the aroma score according to the present embodiment will be described with reference to FIG. 25. FIG. 25 is an explanatory diagram illustrating a configuration example of functional blocks of the generator 800 according to the present embodiment. As illustrated in FIG. 25, the generator 800 according to the present embodiment mainly includes a processing unit 810, a communication unit 830, and a storage unit 840. Hereinafter, each functional block of the generator 800 will be sequentially described.

(Processing Unit 810)

The processing unit 810 can integrally control the operation of the generator 800, and is realized by, for example, a processing circuit such as a CPU. Specifically, the processing unit 810 includes a content acquisition unit 812 that acquires the meta information of the content or the content data itself, and an extraction unit 814 that extracts the meta information or the like from the acquired data. In addition, the processing unit 810 includes a sub-aroma score acquisition unit 816 that acquires the sub-aroma score corresponding to the meta information extracted, and a generation unit 818 that generates the aroma score using the sub-aroma score acquired so as to discharge the aroma in synchronization with output of the content. Furthermore, the processing unit 810 may include a converter 820 that converts the generated aroma score into the one-dimensional or two-dimensional code.

(Communication Unit 830)

The communication unit 830 can transmit and receive information to and from an external device such as the server 700, and for example, can distribute the one-dimensionally or two-dimensionally coded aroma score in association with the identification information of the content. In other words, the communication unit 830 can be a communication interface having a function of transmitting and receiving data.

(Storage Unit 840)

The storage unit 840 stores, for example, the sub-aroma score including a variable-length data array including a plurality of characters or numbers. Note that the storage unit 840 is realized by, for example, a storage device such as an HDD.

<7.2 Processing Method>

Figures 26, 27:
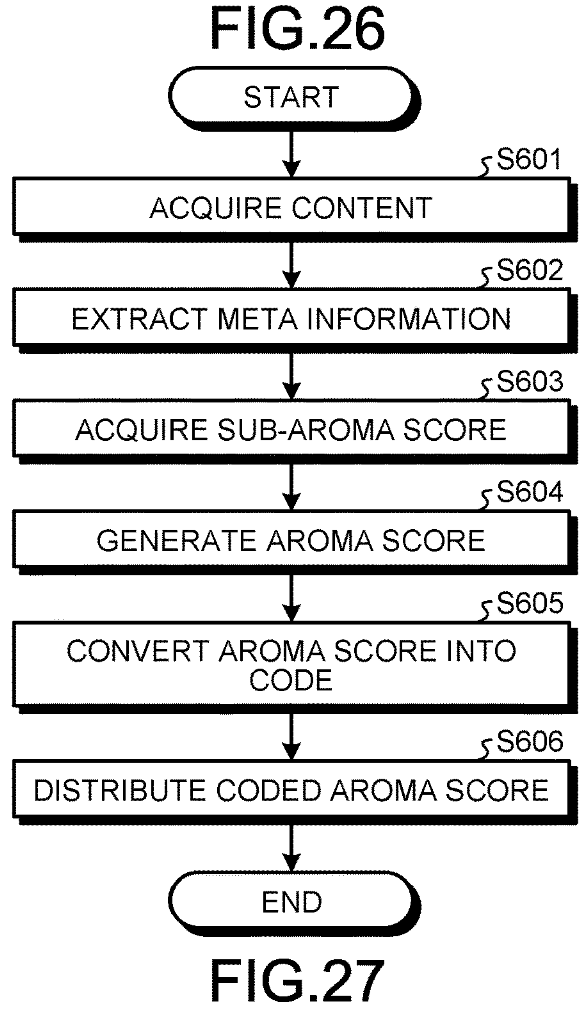
FIG. 26 is a flowchart illustrating an example of a processing method according to the sixth embodiment.
FIG. 27 is an explanatory diagram illustrating a sub-aroma score according to a modification of the sixth embodiment.

Next, the processing method according to the present embodiment will be described with reference to FIG. 26. FIG. 26 is a flowchart illustrating an example of the processing method according to the present embodiment. Specifically, as illustrated in FIG. 26, the processing method according to the present embodiment may include steps from Step S601 to Step S606. Details of these steps according to the present embodiment will be described below.

First, the generator 800 acquires the meta information of the content or the content data itself (Step S601). Next, the generator 800 extracts the meta information and the like from the data acquired in Step S601 (Step S602). Then, the generator 800 acquires the sub-aroma score corresponding to the meta information extracted (Step S603). Further, the generator 800 generates the aroma score using the sub-aroma score acquired in Step S603 described above (Step S604).

Then, the generator 800 converts the aroma score generated in Step S604 described above into a one-dimensional or two-dimensional code (Step S605). Further, the generator 800 distribute the one-dimensionally or two-dimensionally coded aroma score in association with the identification information of the content (Step S606).

As described above, in the present embodiment, the aroma score corresponding to the existing content can be easily generated by generating the aroma score of the content using the sub-aroma score corresponding to the meta information of the content.

<7.3 Modification>

Figure 28:
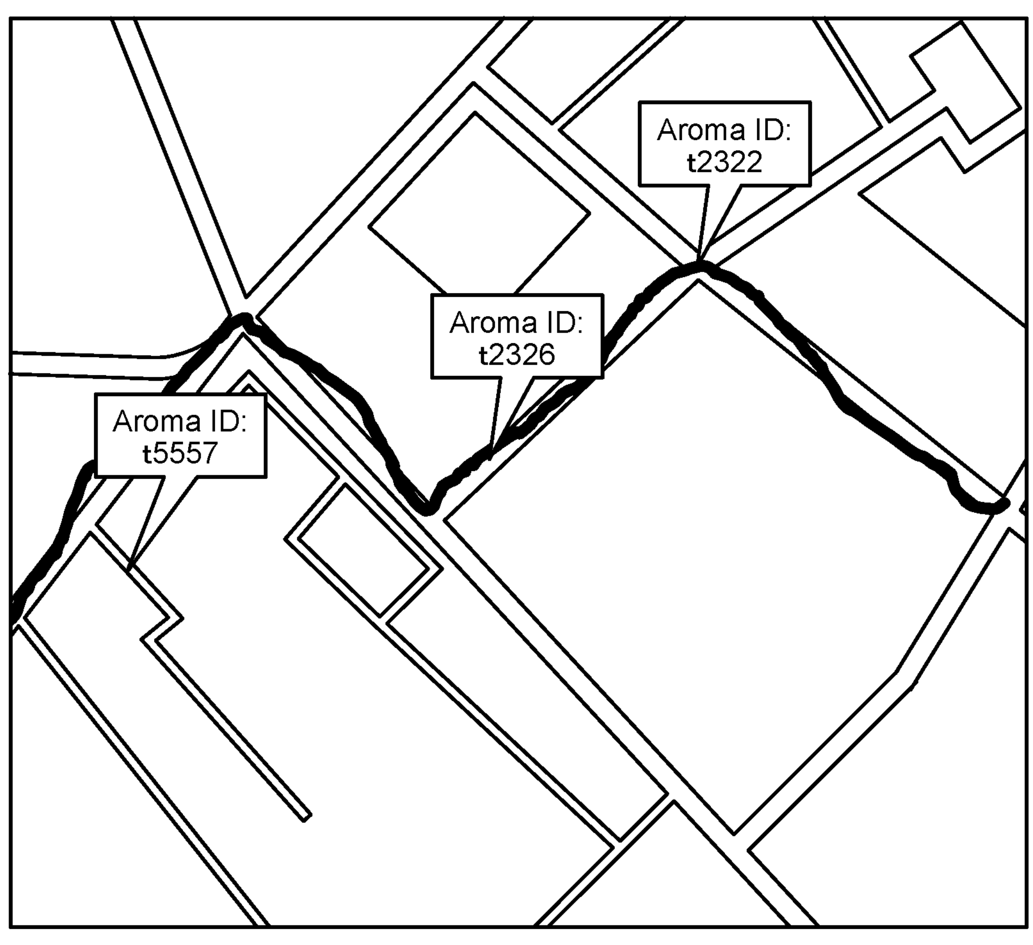
FIG. 28 is an explanatory diagram illustrating a modification of the sixth embodiment.

Furthermore, the present embodiment can be modified as follows. Hereinafter, modifications of the present embodiment will be described with reference to FIGS. 27 and 28. FIG. 27 is an explanatory diagram illustrating the sub-aroma score according to a modification of the present embodiment, and FIG. 28 is an explanatory diagram illustrating another modification of the present embodiment.

First Modification

In the present modification, the above-described extraction unit (word extraction unit) 814 may analyze the content data (reproduction data) of the content including at least sound as the meta information, and extract one or a plurality of words from the sound data included in the content data. In the present modification, the above-described sub-aroma score acquisition unit 816 acquires the sub-aroma score prepared in advance corresponding to the extracted words. For example, when a term "rose" is extracted from the content data, the sub-aroma score acquisition unit 816 acquires the sub-aroma score with aroma of "rose" as illustrated in FIG. 27. Note that, in the present modification, the generation unit 818 generates the aroma score such that the aroma is discharged according to the acquired sub-aroma score at a timing when the word extracted from the content on the time axis appears.

Note that the present modification is not limited to word extraction from the sound data. For example, the extraction unit (object extraction unit) 814 may analyze the content data (reproduction data) of the content including at least a video as the meta information, and extract one or a plurality of objects from video data included in the content data. In this case, the sub-aroma score acquisition unit 816 acquires the sub-aroma score prepared in advance corresponding to the extracted object. For example, when a video of "apple" is extracted from the content data, the sub-aroma score acquisition unit 816 acquires the sub-aroma score with aroma of "apple". Note that, in the present modification, the generation unit 818 generates the aroma score such that the aroma is discharged according to the acquired sub-aroma score at a timing when the video of the object extracted from the content on the time axis appears.

Modification 2

When the content is data associated with the position information, the aroma score can be generated as follows. In the present modification, for example, as illustrated in FIG. 28, it is assumed that a plurality of aroma scores are associated with the position information and registered in a server (not illustrated) in advance. It is assumed that these aroma scores are created, for example, based on aromas picked up when another user visited the site. Then, in the present modification, for example, when the position information of the position where each image is recorded is attached to the content data of the moving image in which the user's own travel is recorded, the aroma scores registered in advance are associated with the position information located at the same position as or in the vicinity of the attached position information, and are acquired as the sub-aroma scores used when generating the aroma score of the content.

8. Summary

As described above, according to each embodiment of the present disclosure, it is possible to easily enjoy the entertainment that presents the fragrance together with the content.

Note that each embodiment of the present disclosure described above is not limited to application to the entertainment or the like that presents the fragrance together with the content, and can be applied to, for example, medical treatment, sleep introduction, relaxation, and the like by catching a predetermined aroma while viewing a predetermined video or music. Furthermore, the device or the like according to each embodiment of the present disclosure can cooperate with a device used in an attraction facility, an educational facility, or the like. In addition, the above description refers to the fragrance presented together with the content, but in each embodiment of the present disclosure, the invention is not limited thereto, and only the fragrance may be presented to the user according to the aroma score.

9. Hardware Configuration

Figure 29:
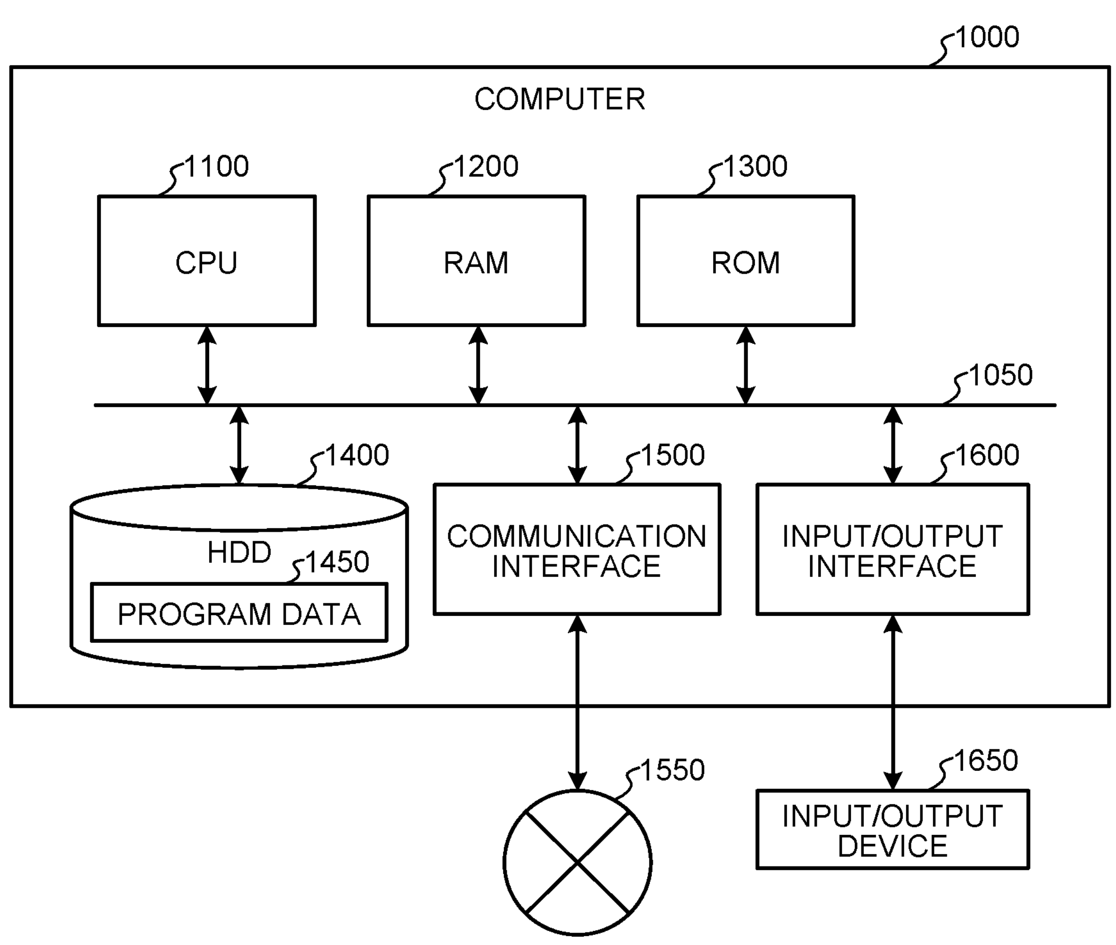

The information processing apparatus such as the information processing terminal 300 according to each embodiment described above is realized by, for example, the computer 1000 having a configuration as illustrated in FIG. 29. Hereinafter, a smart speaker 20 according to the embodiment of the present disclosure will be described as an example. FIG. 29 is a hardware configuration diagram illustrating an example of the computer 1000 that implements functions of the information processing terminal 300 and the like. The computer 1000 includes a CPU 1100, a RAM 1200, a read only memory (ROM) 1300, a hard disk drive (HDD) 1400, a communication interface 1500, and an input/output interface 1600. Each unit of the computer 1000 is connected by a bus 1050.

The CPU 1100 operates based on a program stored in the ROM 1300 or the HDD 1400, and controls each unit. For example, the CPU 1100 develops a program stored in the ROM 1300 or the HDD 1400 into the RAM 1200, and executes processes corresponding to various programs.

The ROM 1300 stores a boot program such as a basic input output system (BIOS) executed by the CPU 1100 when the computer 1000 is activated, a program dependent on hardware of the computer 1000, and the like.

The HDD 1400 is a computer-readable recording medium that non-transiently records a program executed by the CPU 1100, data used by the program, and the like. Specifically, the HDD 1400 is a recording medium that records the information processing program according to the present disclosure, which is an example of program data 1450.

The communication interface 1500 is an interface to connect the computer 1000 with an external network 1550 (e.g., the Internet). For example, the CPU 1100 receives data from another device or transmits data generated by the CPU 1100 to another device via the communication interface 1500.

The input/output interface 1600 is an interface for connecting an input/output device 1650 and the computer 1000. For example, the CPU 1100 receives data from the input/output device 1650 such as a keyboard, a mouse, or a microphone (microphone) via the input/output interface 1600. In addition, the CPU 1100 transmits the data to an output device such as a display, a speaker, or a printer via the input/output interface 1600. Furthermore, the input/output interface 1600 may function as a media interface that reads a program or the like recorded in a predetermined recording medium (medium). The medium is, for example, an optical recording medium such as a digital versatile disc (DVD) or a phase change rewritable disk (PD), a magneto-optical recording medium such as a magneto-optical disk (MO), a tape medium, a magnetic recording medium, a semiconductor memory, or the like.

For example, when the computer 1000 functions as the smart speaker 20 according to the embodiment of the present disclosure, the CPU 1100 of the computer 1000 realizes the functions of the control unit 200 and the like by executing a program stored in the RAM 1200. In addition, the HDD 1400 stores an information processing program and the like according to the present disclosure. Note that the CPU 1100 reads the program data 1450 from the HDD 1400 and executes the program data. As another example, these programs may be acquired from another device via the external network 1550.

Furthermore, the information processing apparatus according to the present embodiment may be applied to a system including a plurality of devices on the premise of connection to a network (or communication between devices), such as cloud computing. In other words, for example, the information processing apparatus according to the present embodiment described above can be implemented as the information processing system according to the present embodiment by a plurality of apparatuses.

The example of the hardware configuration of the information processing terminal 300 and the like has been described above. Each of the above-described components may be configured using a general-purpose member, or may be configured by hardware specialized for the function of each component. This configuration can be appropriately changed according to a technical level at the time of implementation.

10. Supplement

Note that the embodiments of the present disclosure described above may include, for example, the processing method executed by the fragrance presentation device 100 or the fragrance presentation system 10 as described above, the program that causes the device to function, and a non-transitory tangible medium in which the program is recorded. Further, the program may be distributed via a communication line (including wireless communication) such as the Internet.

Furthermore, each step in the processing method of the embodiments of the present disclosure described above may not necessarily be processed in the described order. For example, each step may be implemented in an appropriately changed order. In addition, each step may be partially implemented in parallel or individually instead of being implemented in time series. Furthermore, the process in each step does not necessarily have to be performed according to the described method, and may be performed, for example, by another method by another functional unit.

Although the preferred embodiment of the present disclosure has been described in detail with reference to the accompanying drawings, the technical scope of the present disclosure is not limited to these examples. It is obvious that a person having ordinary knowledge in the technical field of the present disclosure can conceive various changes or modifications within the scope of the technical idea described in the claims, and it is naturally understood that these also belong to the technical scope of the present disclosure.

Furthermore, the effects described in the present specification are merely illustrative or exemplary, and are not restrictive. In other words, the technology according to the present disclosure can exhibit other effects obvious to those skilled in the art from the description of the present specification together with or instead of the above effects.

The present technology can also have the following configurations.

(1) A fragrance presentation device that presents a fragrance in conjunction with content including at least one element of a sound, a music, an image, a video, and a tactile stimulation, the fragrance presentation device comprising:

a housing unit configured to house a cartridge containing an aroma, the aroma being one or a plurality of aromas; and a discharge unit configured to discharge the aroma, wherein the aroma is discharged, according to an aroma score, in synchronization with an output of the content, the aroma score including at least one element of an aroma type, an aroma generation timing, a discharge duration, a discharge amount, a discharge pattern, and a discharge trigger.

(2) The fragrance presentation device according to (1), further comprising:
an acquisition unit configured to acquire the aroma score;
an output unit configured to output the content; and
a control unit configured to control the discharge unit so as to discharge the aroma, according to the aroma score, in synchronization with the output of the content.

(3) The fragrance presentation device according to (2) further comprising
a reader configured to read the aroma score that is one-dimensionally or two-dimensionally coded.

(4) The fragrance presentation device according to (3), wherein the reader reads the aroma score that is one-dimensionally or two-dimensionally coded and printed on a medium storing data of the content or a package of the medium.

(5) The fragrance presentation device according to any one of (1) to (4), wherein the aroma score is linked to the content on a time axis.

(6) The fragrance presentation device according to (2), further comprising:
a biological information acquisition unit configured to acquire biological information of a user at a time of presenting the content; and
an adjustment unit configured to adjust the aroma score according to the biological information, wherein
the control unit controls the discharge unit according to the aroma score adjusted.

(7) The fragrance presentation device according to (2), further comprising:
an environment information acquisition unit configured to acquire environment information around a user at a time of presenting the content; and
an adjustment unit configured to adjust the aroma score according to the environment information, wherein
the control unit controls the discharge unit according to the aroma score adjusted.

(8) The fragrance presentation device according to (7), wherein the environment information acquisition unit acquires at least one of a temperature, a humidity, an air volume, a weather, a place, and a positional relationship with another person around the user.

(9) A fragrance presentation system that presents a fragrance in conjunction with content including at least one element of a sound, a music, an image, a video, and a tactile stimulation, the fragrance presentation system comprising:
a fragrance presentation device and an information processing apparatus, wherein
the fragrance presentation device includes:
a housing unit configured to house a cartridge containing an aroma, the aroma being one or a plurality of aromas, and
a discharge unit configured to discharge the aroma, and
the information processing apparatus includes:
an acquisition unit communicably connected to the fragrance presentation device, and configured to acquire an aroma score including at least one element of an aroma type, an aroma generation timing, a discharge duration, a discharge amount, a discharge pattern, and a discharge trigger,
an output unit configured to output the content, and
a control unit configured to control the discharge unit so as to discharge the aroma, according to the aroma score, in synchronization with an output of the content.

(10) A management device that manages an aroma score used in a fragrance presentation device that presents an aroma in conjunction with content including at least one element of a sound, a music, an image, a video, and a tactile stimulation, the management device comprising
a storage unit configured to store the aroma score, in association with identification information of the content, including information designating at least one element of an aroma type, an aroma generation timing, a discharge duration, a discharge amount, a discharge pattern, and a discharge trigger, the aroma score being a variable-length data array including a plurality of characters or numbers.

(11) The management device according to (10), wherein the storage unit stores the aroma score in association with identification information of a cartridge containing one or a plurality of aromas.

(12) The management device according to (10) or (11), further comprising a distribution unit configured to distribute the aroma score that is one-dimensionally or two-dimensionally coded in association with the identification information of the content.

REFERENCE SIGNS LIST

10 FRAGRANCE PRESENTATION SYSTEM
100, **100*a*, 200** FRAGRANCE PRESENTATION DEVICE
102, **102*a*, 302, 402** AROMA SCORE ACQUISITION UNIT
104, 204 CARTRIDGE HOUSING UNIT
106, 206 DISCHARGE UNIT
**106*a*** DISCHARGE PORT
108 READER
110, 310, 410, 510, 610, 710 CONTROL UNIT
112, 312, 412, 812 CONTENT ACQUISITION UNIT
114, 314, 414, 702, 840 STORAGE UNIT
120, 320, 520 DISPLAY UNIT
122, 322, 522 SOUND OUTPUT UNIT
230, 330, 430, 530, 630 I/F UNIT
300, **300*a*** INFORMATION PROCESSING TERMINAL
318 ADJUSTMENT UNIT
400 GAME MACHINE
500 HMD
600 BIOLOGICAL INFORMATION SENSOR
640 SENSOR UNIT
700 SERVER
704 DB
706, 810 PROCESSING UNIT
712 CLASSIFICATION UNIT
720, 830 COMMUNICATION UNIT
800 GENERATOR
814 EXTRACTION UNIT
816 SUB-AROMA SCORE ACQUISITION UNIT
818 GENERATION UNIT
820 CONVERTER
900 CARTRIDGE
902 AROMA SCORE
904 PACKAGE

The invention claimed is:

1. A fragrance presentation device, comprising:
a housing unit configured to house a cartridge that includes an aroma of a plurality of aromas;
a discharge unit configured to discharge the aroma;
an output unit configured to output content that includes at least one of a sound, a music, an image, a video, or a tactile stimulation;
an acquisition unit configured to acquire an aroma score associated with the content, wherein the acquired aroma score includes at least one of:
an aroma type associated with the content,
an aroma generation timing associated with the content,
a discharge duration associated with the content,
a discharge amount associated with the content,
a discharge pattern associated with the content, or
a discharge trigger associated with the content;
a biological information acquisition unit configured to acquire user biological information at a time of the output of the content;
an adjustment unit configured to adjust the acquired aroma score based on the acquired user biological information; and
a control unit configured to control, based on the adjusted aroma score, the discharge unit to discharge the aroma, wherein the discharge of the aroma is in synchronization with the output of the content.

2. The fragrance presentation device according to claim 1, further comprising a reader configured to read the aroma score that is one of one-dimensionally coded data or two-dimensionally coded data, wherein the acquisition of the aroma score is based on the read aroma score.

3. The fragrance presentation device according to claim 2, wherein
the one of the one-dimensionally coded data or the two-dimensionally coded data is on one of a medium or a package of the medium, and
the medium stores data of the content.

4. The fragrance presentation device according to claim 1, wherein the acquired aroma score is linked to the content on a time axis.

5. The fragrance presentation device according to claim 1, further comprising an environment information acquisition unit configured to acquire, at the time of the output of the content, environment information associated with a first user, wherein the adjustment unit is further configured to adjust the acquired aroma score based on the acquired environment information.

6. The fragrance presentation device according to claim 5, wherein
the environment information acquisition unit is further configured to acquire at least one of:
a temperature associated with the first user,
a humidity associated with the first user,
an air volume associated with the first user,
a weather associated with the first user,
a place associated with the first user, or
a positional relationship of the first user with a second user, and
the second user is in a vicinity of the first user.

7. A fragrance presentation system, comprising:
a fragrance presentation device; and
an information processing apparatus connected to the fragrance presentation device, wherein
the fragrance presentation device includes:
a housing unit configured to house a cartridge that includes an aroma of a plurality of aromas; and
a discharge unit configured to discharge the aroma,
the information processing apparatus includes:
an output unit configured to output content that includes at least one of a sound, a music, an image, a video, or a tactile stimulation;
an acquisition unit configured to acquire an aroma score associated with the content, wherein the acquired aroma score includes at least one of:
an aroma type associated with the content,
an aroma generation timing associated with the content,
a discharge duration associated with the content,
a discharge amount associated with the content,
a discharge pattern associated with the content, or
a discharge trigger associated with the content;
a biological information acquisition unit configured to acquire user biological information at a time of the output of the content;
an adjustment unit configured to adjust the acquired aroma score based on the acquired user biological information; and
a control unit configured to control, based on the adjusted aroma score, the discharge unit to discharge the aroma, and
the discharge of the aroma is in synchronization with the output of the content.

8. A management device, comprising:
a storage unit configured to store an aroma score associated with a fragrance presentation device, wherein
the fragrance presentation device presents, based on the aroma score, an aroma in synchronization with content,
the content includes at least one of a sound, a music, an image, a video, or a tactile stimulation,
the storage of the aroma score is in association with identification information of the content,
the identification information of the content includes a management number of the content,
the stored aroma score includes information that designates at least one of:
an aroma type associated with the content,
an aroma generation timing associated with the content,
a discharge duration associated with the content,
a discharge amount associated with the content,
a discharge pattern associated with the content, or
a discharge trigger associated with the content,
the stored aroma score is a variable-length data array, and
the variable-length data array includes at least one of a plurality of characters or a plurality of numbers.

9. The management device according to claim 8, wherein
the storage unit is further configured to store the aroma score in association with identification information of a cartridge,
the cartridge includes a plurality of aromas, and
the plurality of aromas includes the aroma.

10. The management device according to claim 8, further comprising a distribution unit, wherein
the stored aroma score is one of:
one-dimensionally coded in association with the identification information of the content, or
two-dimensionally coded in association with the identification information of the content, and
the distribution unit is configured to distribute the stored aroma score.

* * * * *